United States Patent
Hajitou et al.

(10) Patent No.: US 10,799,542 B2
(45) Date of Patent: Oct. 13, 2020

(54) TETRAFUNCTIONAL BACTERIOPHAGE

(71) Applicant: Imperial College Innovations Limited, London (GB)

(72) Inventors: Amin Hajitou, London (GB); Teerapong Yata, London (GB)

(73) Assignee: Imperial College Innovations Limited, London (GB)

(*) Notice: Subject to any disclaimer, the term of this patent is extended or adjusted under 35 U.S.C. 154(b) by 214 days.

(21) Appl. No.: 14/889,805

(22) PCT Filed: May 12, 2014

(86) PCT No.: PCT/GB2014/051446
§ 371 (c)(1),
(2) Date: Nov. 6, 2015

(87) PCT Pub. No.: WO2014/184528
PCT Pub. Date: Nov. 20, 2014

(65) Prior Publication Data
US 2017/0340684 A1  Nov. 30, 2017

(30) Foreign Application Priority Data
May 15, 2013 (GB) .................................. 1308742.4

(51) Int. Cl.
*A61K 35/76* (2015.01)
*C12N 15/86* (2006.01)

(52) U.S. Cl.
CPC .............. *A61K 35/76* (2013.01); *C12N 15/86* (2013.01); *C07K 2319/00* (2013.01);
(Continued)

(58) Field of Classification Search
None
See application file for complete search history.

(56) References Cited

U.S. PATENT DOCUMENTS

2003/0113293 A1* 6/2003 Bermudes .............. A61K 48/00
424/93.2
2004/0048243 A1  3/2004 Arap et al.
(Continued)

FOREIGN PATENT DOCUMENTS

WO  1999010014 A2  3/1999
WO  WO 99/10014  * 3/1999  .............. A61K 48/00
(Continued)

OTHER PUBLICATIONS

Kia et al. Dual systemic tumor targeting with ligand-directed phage and Grp78 promoter induces tumor regression. Mol Cancer Ther. Dec. 2012;11(12):2566-77. (Year: 2012).*
(Continued)

*Primary Examiner* — Michelle S Horning
(74) *Attorney, Agent, or Firm* — Linda B. Huber; Nixon Peabody LLP

(57) ABSTRACT

The invention provides a recombinant targeted bacteriophage for expressing a transgene in a target cell transduced with the bacteriophage. The bacteriophage comprises a first nucleic acid sequence encoding a pIII capsid minor coat protein that is configured to display a cell-targeting ligand for enabling delivery of the bacteriophage to a target cell, a second nucleic acid sequence encoding at least one pVIII capsid major coat protein that is configured to display a foreign peptide thereon, and a transgene which encodes a protein which exerts a biological effect on the target cell.

13 Claims, 13 Drawing Sheets

Figure 1:
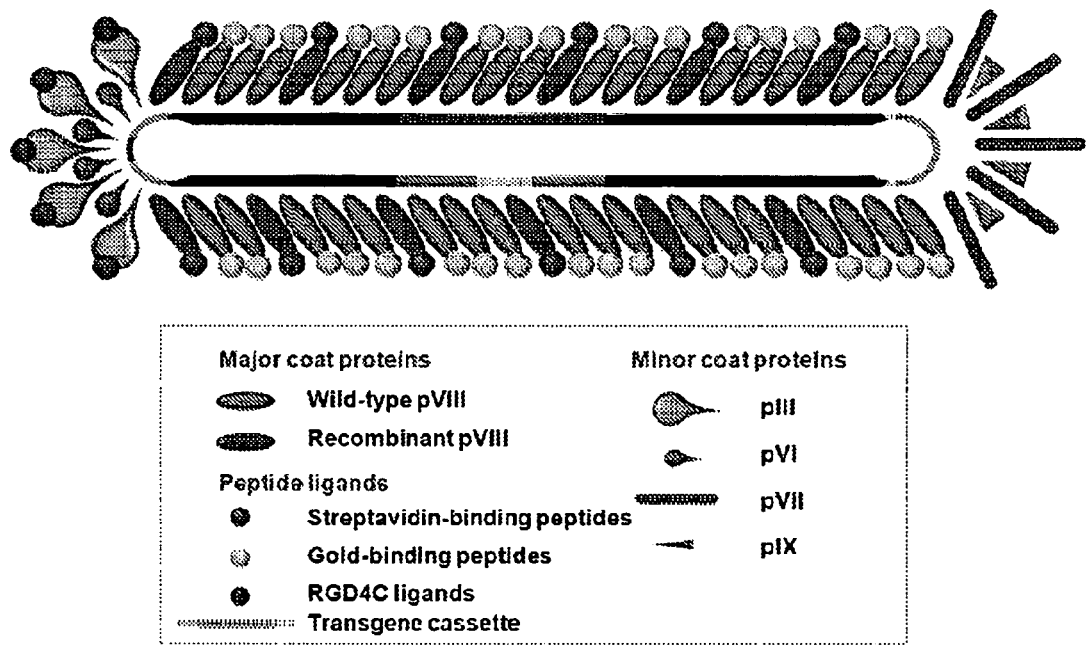

Specification includes a Sequence Listing.

(52) U.S. Cl.
CPC ...... *C07K 2319/09* (2013.01); *C07K 2319/74* (2013.01); *C12N 2795/10043* (2013.01); *C12N 2795/10045* (2013.01)

(56) References Cited

U.S. PATENT DOCUMENTS

| | | | |
|---|---|---|---|
| 2005/0112550 A1* | 5/2005 | Gershoni | C12N 15/1037 435/5 |
| 2006/0105387 A1* | 5/2006 | Prior | C07K 14/79 435/7.1 |
| 2016/0114032 A1 | 4/2016 | Hajitou et al. | |
| 2019/0083610 A1 | 3/2019 | Hajitou et al. | |

FOREIGN PATENT DOCUMENTS

| | | |
|---|---|---|
| WO | 2002081635 A2 | 10/2002 |
| WO | 2003/077953 A2 | 9/2003 |
| WO | 2006095345 A2 | 9/2006 |
| WO | 2009024591 A1 | 2/2009 |
| WO | 2014184528 A1 | 11/2014 |
| WO | 2014184529 A1 | 11/2014 |

OTHER PUBLICATIONS

Hirosue et al. pH-Dependent lytic peptides discovered by phage display. Biochemistry. May 23, 2006;45(20):6476-87. (Year: 2006).*

Baker et al., Protein Structure Predication and Structural Genomics, Science (2001) vol. 294, No. 5540, pp. 93-96 (Year: 2001).*

Attwood, T. The Babel of Bioinformatics, Science (2000) vol. 290, No. 5491, pp. 471-473 (Year: 2000).*

Akuta et al. Enhancement of phage-mediated gene transfer by nuclear localization signal. Biochem Biophys Res Commun. Oct. 4, 2002;297(4):779-86. (Year: 2002).*

Ashley et al. Cell-specific delivery of diverse cargos by bacteriophage MS2 virus-like particles. ACS Nano. Jul. 26, 2011;5(7):5729-45. (Year: 2011).*

Lamboy et al. Chemical and genetic wrappers for improved phage and RNA display. Chembiochem. Nov. 24, 2008;9(17):2846-52. (Year: 2008).*

GenBank: AF218364 filamentous phage display vector fUSE5 (Year: 2000).*

GenBank: AF218363 filamentous phage display vector f88-4 (Year: 2000).*

PCT/GB2014/051446 International Search Report and Written Opinion dated Jul. 30, 2014; 15 pages.

PCT/GB2014/051447 International Search Report and Written Opinion dated Sep. 3, 2014; 12 pages.

Aujame et al., Experimental Design Optimization of Filamentous Phage Transfection into Mammalian Cells by Cationic Lipids, BioTechniques, 2000, vol. 28, pp. 1202-1213.

Chen et al., Cancer Gene Therapy by Direct Tumor Injections of a Nonviral T7 Vector Encoding a Thymidine Kinase Gene, Human Gene Therapy, 1998, vol. 9, pp. 729-736.

Chung et al. Fabrication of engineered M13 bacteriophages into liquid crystalline films and fibers for directional growth and encapsulation of fibroblasts. Soft Matter (2010). 6(18): 4454-4456.

Greenstein et al. Indroduction to vectors derived from filamentous phages. Curr Protoc Mol Biol (2001). Ch. 1: Unit 1.14, p. 15.

Groot-Wassink, T. Quantitative Imaging of Na/I Symporter Transgene Expression Using Positron Emission Tomography in the Living Animal. Molecular Therapy (2004). 9(3):436-442.

Guo et al. Construction of bifunctional phage display for biological analysis and immunoassay. Anal Biochem (2010). 396(1):155-157.

Hajitou et al. A hybrid vector for ligand-directed tumor targeting and molecular imaging. Cell (2006). 125(2):385-98.

Hirosue et al. pH-Dependent lytic peptides discovered by phage display. Biochemistry (2006). 45(20):6476-6487.

Ishiura et al., Phage Particle-Mediated Gene Transfer to Cultured Mammalian Cells, Molecular and Cellular Biology, 1982, vol. 2(6), pp. 607-616.

Kia et al. Dual Systemic Tumor Targeting with Ligand-Directed Phage and Grp78 Promoter Induces Tumor Regression. Molecular Cancer Therapeutics (2012). 11(12):2566-2577.

Lamboy et al., Phage Wrapping with Cationic Polymers Eliminates Non-Specific Binding between M13 Phage and High pI Target Proteins, J Am Chem Soc., 2009, vol. 131(45), pp. 16454-16460.

Larocca et al. Targeting Bacteriophage to Mammalian Cell Surface Receptors for Gene Delivery. Human Gene Therapy (1998). 9:2393-2399.

Prisco et al. Filamentous Bacteriophage Fd as an Antigen Delivery System in Vaccination. International Journal of Molecular Sciences (2012). 13(12):5179-5194.

Rangel et al. Combinatorial targeting and discovery of ligand-receptors in organelles of mammalian cells. Nat Commun (2012). 3:788, 10 pages.

Sartorius et al. Vaccination with filamentous bacteriophages targeting DEC-205 induces DC maturation and potent anti-tumor T-cell responses in the absence of adjuvants. Eur J Immunol (2011). 41:2573-2584.

Scott et al. Searching for Peptide Ligands with an Epitope Library. Science (1990). 249:386-390.

Scott et al. EBI Accession No. EMBL: AAF78530. Filamentous phage display vector f88-4 recombinant major coat protein precursor. (2000). 1 pages.

Sidhu et al., Phage Display in Phamaceutical Biotechnology, Current Opinion in Biotechnology, 2000, vol. 11, pp. 610-616.

Van Houten et al. Filamentous phage as an immunogenic carrier to elicit focused antibody responses against a synthetic peptide. Vaccine (2006). 24(19):4188-4200.

Zecchin et al., Transfection and DNA-Mediated Gene Transfer, Methods of Molecular Biology, 2011, vol. 731, pp. 435-450.

* cited by examiner a)

b)

Incubation time of phage with fribrinogen (min)

Antibody dilution

TETRAFUNCTIONAL BACTERIOPHAGE

CROSS-REFERENCE TO RELATED APPLICATIONS

This application is a National Phase of International Application No. PCT/GB2014/051446 filed May 12, 2014, currently pending, which designated the U.S. and that International Application was published under PCT Article 21(2) in English. This application also includes a claim of priority under 35 U.S.C. 119(a) and § 365(b) to British patent application No. GB 1308742.4 filed May 15, 2013, now expired, the entirety of which is hereby incorporated by reference.

The present invention relates to bacteriophages, and, in particular to novel multifunctional bacteriophages, and their uses for the delivery of transgenes in a variety of gene therapy applications, vaccine delivery and imaging techniques, as well as the simultaneous expression of functional foreign proteins, peptides, antigens or antibodies displayed on the capsid of the multifunctional bacteriophage.

Despite their attractive features and advanced knowledge of their molecular biology, bacteriophage viruses are still considered to be poor vectors for gene transfer limiting their application in a broad range of disciplines including gene therapy and DNA vaccine delivery. It is clear that phage has evolved to infect bacteria only and has no optimized strategies to transfer and express transgenes in mammalian cells. Previous work has shown that phage gene transfer efficacy is amenable to evolve and that one efficient strategy is to combine bacteriophage with the attributes of animal viruses. For example, incorporating the genetic cis-elements ITR from the animal virus AAV-2 into the phage genome resulted in altered transgene cassette and subsequent enhanced gene delivery efficacy of bacteriophage.

However, to date most progress in advancing bacteriophage as a vector has been made at the genome level, which is one last step of a series of phases involved in a gene transfer process. Indeed, it is well-established that gene delivery efficiency depends on the efficacy of the vector to complete a succession of steps. Firstly, the vector needs to access the cell surface to bind to its receptor to allow internalization in cells. Secondly, the vector has to escape from endosomes and be released into the cytoplasm. Thirdly, the vector must then be transported to the nucleus for gene expression to occur. To date, current bacteriophage-based vectors are unable to efficiently overcome these obstacles in transgene expression.

Accordingly, there is therefore a need to provide an improved bacteriophage-driven gene delivery vector system, which efficiently and specifically delivers transgenes to target cells of interest in vivo. The inventors postulated that the ideal bacteriophage vector would be a phage that is capable of combining multiple strategies for resolving the mammalian cell barriers into a single viral particle, in addition to effecting transgene expression. The inventors have therefore developed a novel multifunctional bacteriophage based on the targeted M13 filamentous bacteriophage, which exhibits a number of novel functionalities.

Hence, according to a first aspect of the invention, there is provided a recombinant targeted bacteriophage for expressing a transgene in a target cell transduced with the bacteriophage, the bacteriophage comprising a first nucleic acid sequence encoding a pIII capsid minor coat protein that is configured to display a cell-targeting ligand for enabling delivery of the bacteriophage to a target cell, a second nucleic acid sequence encoding at least one pVIII capsid major coat protein that is configured to display a foreign peptide thereon, and a transgene which encodes a protein which exerts a biological effect on the target cell.

It will be appreciated that bacteriophages (i.e. phages) are viruses that infect and replicate within bacteria. The advantage of using bacteriophages as gene delivery vectors, as opposed to other regular viruses, is that they do not naturally infect non-bacterial cells, such as mammalian cells, unless they are genetically modified to specifically do so. As described in the Examples, the inventors have designed a highly effective and novel multifunctional bacteriophage in accordance with the first aspect, which is based on a targeted M13 RGD4C-phage, and which simultaneously carries out multiple functions. Advantageously, the bacteriophage of the invention comprises a pIII minor coat protein which displays the cell-targeting ligand (e.g. RGD4C), which enables highly targeted delivery to the target cell, for example a tumour cell.

Furthermore, the bacteriophage of the invention enables the display of large foreign functional peptides on its surface via the pVIII major coat protein. In addition, the phage also enables expression, in the target cell (or tissue) that has been transduced with the phage, of the transgene, which is preferably inserted in an intergenomic region of the bacteriophage's genome.

To date, there have been no reports of using a bacteriophage to deliver a transgene to a target cell, in which the phage comprises one or more pVIII capsid major coat proteins for display foreign peptides thereon. The advantage of constructing a targeted bacteriophage with more than one pVIII major coat protein is that (i) it provides the choice to use one pVIII major coat protein for the display of large foreign peptide or proteins while keeping the wild type pVIII intact, which is important to achieve efficient phage assembly and subsequently high titers of the phage vector, (ii) it allows the display of a considerable copy number of the peptide in order to yield a phage which displays hundreds or even thousands of functional foreign peptides, and (iii) it offers the possibility of the simultaneous display of two different functional peptides on the capsid of a single bacteriophage particle. It will be appreciated that a foreign peptide or protein is one that is not normally or naturally expressed by the phage, i.e. it can be heterologous. This new class of targeted multifunctional phage will advance targeted gene and peptide delivery in a broad range of applications, including gene therapy, DNA vaccines and imaging techniques.

Examples of the bacteriophage preferably include any negatively charged bacteriophage, and more preferably one of the filamentous phages, such as F1, Fd or M13. However, a most preferred bacteriophage according to the invention is M13.

As described in the Examples, the inventors have developed a novel M13-based phage based on (i) the fUSE5 phage, the sequence of which is found at GenBank Accession Number AF218364, and (ii) the f88.4 phage, the sequence of which is found at GenBank Accession Number: AF218363. The fUSE5 phage comprises a single gene encoding a major coat protein pVIII, whereas the f88.4 phage comprises two genes encoding two different embodiments of the pVIII protein, namely wild-type and recombinant pVIII. A fragment containing the recombinant pVIII gene, preferably under the control of a tac promoter, was removed from the f88.4 phage and inserted into an intergenomic region of the fUSE5 phage to generate a bacteriophage harbouring two pVIII genes.

Therefore, in one embodiment, the second nucleic acid sequence encodes a wild-type pVIII capsid major coat protein. The DNA sequence encoding one embodiment of a wild-type pVIII capsid major coat protein is represented herein as SEQ ID No: 1, as follows:

[SEQ ID NO: 1]
atgaaaaagtctttagtcctcaaagcctccgtagccgttgctaccctcgt tccgatgctgtctttcgctgctgagggtgacgatcccgcaaaagcggcct ttgactccctgcaagcctcagcgaccgaatatatcggttatgcgtgggcg atggttgttgtcattgtcggcgcaactatcggtatcaagctgtttaagaa attcacctcgaaagcaagctga Accordingly, preferably the second nucleic acid sequence encoding a wild-type pVIII capsid major coat protein comprises a nucleotide sequence substantially as set out in SEQ ID No: 1, or a functional variant or fragment thereof.

One embodiment of the polypeptide sequence of a wild-type pVIII capsid major coat protein is provided herein as SEQ ID No: 2, as follows:

[SEQ ID NO: 2]
MKKSLVLKASVAVATLVPMLSFAAEGDDPAKAAFDSLQASATEYIGYAWA

MVVVIVGATIGIKLFKKFTSKAS-

Accordingly, preferably the wild-type pVIII capsid major coat protein comprises an amino acid sequence substantially as set out in SEQ ID No: 2, or a functional variant or fragment thereof.

In another embodiment, the second nucleic acid sequence encodes a recombinant pVIII capsid major coat protein. The DNA sequence encoding one embodiment of a recombinant pVIII capsid major coat protein is represented herein as SEQ ID No: 3, as follows:

[SEQ ID NO: 3]
atgaaaaagtctttagttcttaaagcatctgttgctgttgcgactcttgt tcctatgctaagctttgccaacgtcctgcagaaggtgatgaccggcta aagctgcttttgactctcttcaggcttctgctactgaatacatcggctac gcttgggctatggtggttgttatcgttggtgctactattggcatcaaact tttcaaaaattcacttctaaagcgtcttaa Accordingly, in one embodiment, the second nucleic acid sequence encoding a recombinant pVIII capsid major coat protein comprises a nucleic acid sequence substantially as set out in SEQ ID No:3, or a functional variant or fragment thereof One embodiment of the polypeptide sequence of a recombinant pVIII capsid major coat protein is provided herein as SEQ ID No: 4, as follows:

[SEQ ID NO: 4]
MKKSLVLKASVAVATLVPMLSFANVPAEGDDPAKAAFDSLQASATEYIGY

AWAMVVVIVGATIGIKLFKKFTSKAS-

Accordingly, preferably the recombinant pVIII capsid major coat protein comprises an amino acid sequence substantially as set out in SEQ ID No:4, or a functional variant or fragment thereof.

The recombinant gene VIII is synthetic and differs in nucleotide sequence from the wild-type gene (though it largely encodes the wild-type amino acid sequence). The only difference between the two proteins of SEQ ID No. 2 and 4 is an additional three amino acid sequence (NVP) in the recombinant pVIII (SEQ ID No. 4). The inventors have found that, advantageously, having both the wild-type and the recombinant pVIII capsid major coat protein gives the ability to display a wide range of different foreign proteins each of differing sizes. Indeed, both recombinant and wild type pVIII should allow the display of large peptides, but display of more than 10 amino acid long peptides can have a tendency to affect the ability of the pVIII to support phage assembly and production. Therefore, one solution to overcome this is to construct a phage in which the genome bears two VIII genes, encoding two different types of pVIII molecule. The recombinant gene VIII is synthetic and differs in nucleotide sequence from the wild-type gene (though it largely encodes the wild-type amino acid sequence). This allows hybrid pVIII proteins with quite large foreign peptides to be displayed on the virion surface. Thus, one pVIII (i.e. recombinant pVIII) is used to display large peptide inserts, and the other one (i.e. wild type pVIII) is used to support phage assembly or for the display of small peptide inserts. Therefore, it is possible to design different bacteriophages of the invention, depending on which foreign proteins need to be displayed on the outer capsid.

Therefore, in a preferred embodiment, the bacteriophage of the invention comprises a second nucleic acid sequence which encodes the wild-type pVIII capsid major coat protein and third nucleic acid sequence which encodes a recombinant pVIII capsid major coat protein, or vice versa. Hence, the bacteriophage preferably comprises a nucleic acid sequence substantially as set out in SEQ ID No: 1 and 3, or a functional variant or fragment thereof. In addition, preferably the bacteriophage comprises a wild-type and a recombinant pVIII capsid major coat protein which comprise an amino acid sequence substantially as set out in SEQ ID No: 2 and 4, or a functional variant or fragment thereof.

Preferably, the wild-type pVIII capsid major coat protein and/or the recombinant pVIII capsid major coat protein is configured to display a foreign peptide thereon. Preferably, a nucleic acid encoding the foreign peptide is fused in frame with the pVIII coding gene.

Figure 2:
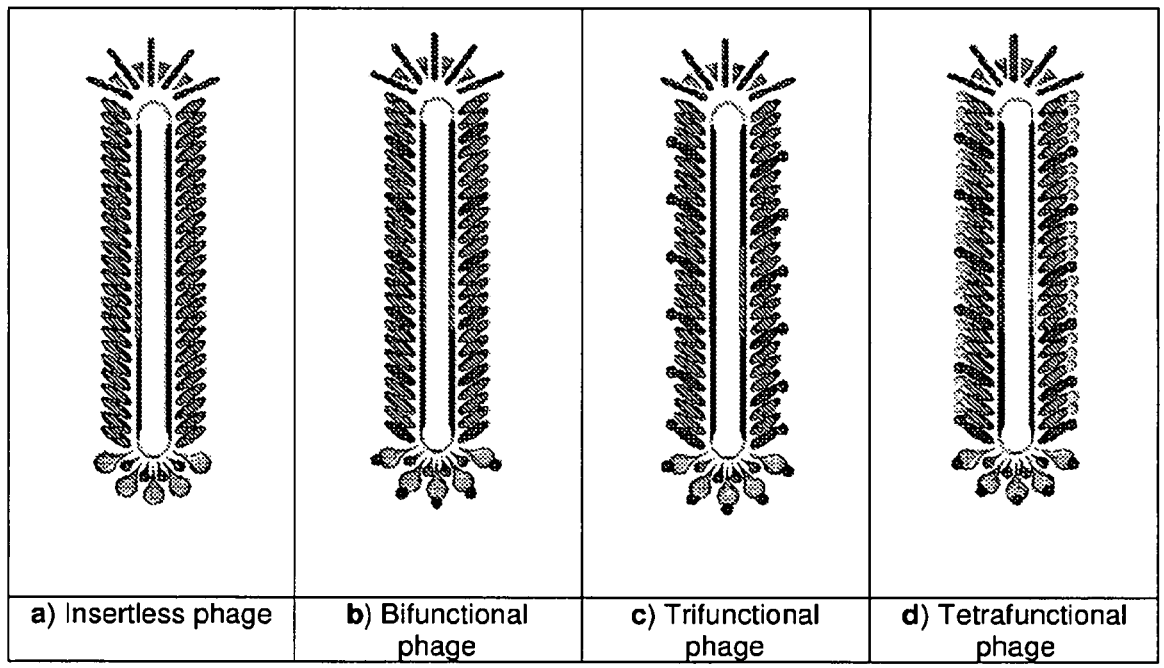

To show that the display of foreign peptides on the pVIII major coat proteins remains intact and functional in the context of the multifunctional phage, the inventors have constructed a phage displaying the two well-characterized peptides, i.e. a streptavidin-binding peptide and a gold-binding peptide, as illustrated in FIGS. 1 and 2. Accordingly, in one embodiment, the pVIII capsid major coat protein is preferably configured to display a streptavidin-binding peptide. For example, the amino acid sequence of the streptavidin-binding peptide may comprise ANRLCHPQFPCT-SHE [SEQ ID No: 5], or a functional fragment or variant thereof. Since this peptide comprises over ten amino acids, it is preferred that the coding sequence of the streptavidin-binding peptide is fused in frame with the recombinant pVIII coding gene.

In another embodiment, the pVIII capsid major coat protein is preferably configured to display a gold-binding peptide. For example, the amino acid sequence of the gold-binding peptide may comprise VSGSSPDS [SEQ ID No: 6], or a functional fragment or variant thereof. Since this peptide comprises less than ten amino acids, the coding sequence of the gold-binding peptide is preferably fused in frame with the wild-type pVIII coding gene. However, this peptide may be displayed on the recombinant pVIII capsid major coat protein, where two short peptides (i.e. less than ten amino acids) are displayed.

In addition to providing the wild-type pVIII major coat protein, the fUSE5 phage also comprises a gene which encodes a pIII capsid minor coat protein on which the cell-targeting ligand may be displayed. The choice of cell-targeting ligand depends on the target cell, which will depend on the specification application of the phage, be it therapeutic, in vaccine delivery or in imaging. By way of example only, in embodiments where the bacteriophage is used to treat cancer, the cell-targeting ligand may be a tumour-targeting ligand. By way of example, in one embodiment, the ligand may comprise the RGD4C ligand (see the Examples), which will be known to the skilled person. It will be appreciated that a phage displaying the cyclic RGD4C (CDCRGDCFC) peptide ligand targets overexpressed c integrin receptors found in tumours. Hence, the RGD4C ligand is a suitable cell-targeting ligand for targeting cancer cells and tumours in general.

Accordingly, the bacteriophage cell-targeting ligand displayed on the pIII capsid minor coat protein is specific for a protein (e.g. a receptor) expressed on the target cell/tissue, so as to enable targeted delivery of the phage thereto. The DNA sequence encoding one embodiment of a pIII capsid minor coat protein is represented herein as SEQ ID No: 7, as follows:

[SEQ ID NO: 7]
gtgaaaaaattattattcgcaattcctttagttgttcctttctattctca ctcggccgtggcgtgcgattgccgcggcgattgcttctgcggcgcggggg ccgaaactgttgaaagttgtttagcaaaacctcatacagaaaattcattt actaacgtctggaaagacgacaaactttagatcgttacgctaactatga gggctgtctgtggaatgctacaggcgttgtggtttgtactggtgacgaaa ctcagtgttacggtacatgggttcctattgggcttgctatccctgaaaat gagggtggtggctctgagggtggcggttctgagggtggcggttctgaggg tggcggtactaaacctcctgagtacggtgatacacctattccgggctata cttatatcaaccctctcgacggcacttatccgcctggtactgagcaaaac cccgctaatcctaatccttctcttgaggagtctcagcctcttaatacttt catgtttcagaataataggttccgaaataggcagggtgcattaactgttt atacgggcactgttactcaaggcactgaccccgttaaaacttattaccag tacactcctgtatcatcaaaagccatgtatgacgcttactggaacggtaa attcagagactgcgctttccattctggctttaatgaggatccattcgttt gtgaatatcaaggccaatcgtctgacctgcctcaacctcctgtcaatgct ggcggcggctctggtggtggttctggtggcggctctgagggtggcggctc tgagggtggcggttctgagggtggcggctctgagggtggcggttccggtg gcggctccggttccggtgattttgattatgaaaaaatggcaaacgctaat aaggggctatgaccgaaaatgccgatgaaaacgcgctacagtctgacgc taaaggcaaacttgattctgtcgctactgattacggtgctgctatcgatg -continued
gtttcattggtgacgtttccggccttgctaatggtaatggtgctactggt gattttgctggctctaattcccaaatggctcaagtcggtgacggtgataa ttcacctttaatgaataatttccgtcaatatttaccttctttgcctcagt cggttgaatgtcgcccttatgtctttggcgctggtaaaccatatgaattt tctattgattgtgacaaaataaacttattccgtggtgtctttgcgtttct tttatatgttgccacctttatgtatgtattttcgacgtttgctaacatac tgcgtaataaggagtcttaa Accordingly, preferably the first nucleic acid sequence encoding the pIII capsid minor coat protein comprises a nucleic acid sequence substantially as set out in SEQ ID No: 7, or a functional variant or fragment thereof.

One embodiment of the polypeptide sequence of a pIII capsid minor coat protein is provided herein as SEQ ID No: 8, as follows:

[SEQ ID NO: 8]
VKKLLFAIPLVVPFYSHSVACDCRGDCFCGAGAETVESCLAKPHTENSFT

NVWKDDKTLDRYANYEGCLWNATGVVVCTGDETQCYGTWVPIGLAIPENE

GGGSEGGGSEGGGSEGGGTKPPEYGDTPIPGYTYINPLDGTYPPGTEQNP

ANPNPSLEESQPLNTFMFQNNRFRNRQGALTVYTGTVTQGTDPVKFYYQY

TPVSSKAMYDAYWNGKFRDCAFHSGFNEDPFVCEYQGQSSDLPQPPVNAG

GGSGGGSGGGSEGGSEGGSEGGSEGGSEGGSEGGSEGGSEGGSEGGSEGGSEGGSGGGSGDFDYEKMANANK

GAMTENADENALQSDAKGKLDSVATDYGAAIDGFIGDVSGLANGNGATGD

FAGSNSQMAQVGDGDNSPLMNNFRQYLPSLPQSVECRPYVPGAGKPYEFS

IDCDKINLPRGVFAPLLYVATFMVYFSTFANILRNKES-

Accordingly, preferably the pIII capsid minor coat protein comprises an amino acid sequence substantially as set out in SEQ ID No: 8, or a functional variant or fragment thereof.

Hence, in a preferred embodiment, the bacteriophage of the first aspect comprises a first nucleic acid sequence encoding a pIII capsid minor coat protein that is configured to display a cell-targeting ligand for enabling delivery of the phage to a target cell, a second nucleic acid sequence encoding a wild type pVIII capsid major coat protein, a third nucleic acid sequence encoding a recombinant pVIII capsid major coat protein, wherein either or both of the major coat proteins is configured to display a foreign peptide thereon, and a transgene which encodes a protein which exerts a biological effect on the target cell.

Advantageously, it will be appreciated therefore that the bacteriophage of the invention can be described as being multifunctional, because it: (i) displays the targeting ligand on the pIII minor coat protein of the phage for binding to a target cell, e.g. a protein or a receptor; (ii) serves as a genetic carrier for (shorter) foreign functional peptides to be displayed on the wild-type pVIII major coat protein in order to operate as a nanoparticle decorated by hundreds of peptides; (iii) allows the display of (larger) foreign peptides on the virion surface by the recombinant pVIII protein; and finally (iv) harbours a transgene cassette inserted in an intergenomic region of the bacteriophage genome for gene expression in target cells.

The transgene may be any gene encoding a protein, which may have therapeutic or industrial utility in the target cell. For example, in embodiments where the phage is used to treat cancer, the transgene may encode the Herpes simplex virus tyrosine kinase gene, which may subsequently exert a therapeutic effect on the target cell. The inventors have demonstrated that the bacteriophage of the invention can be efficiently targeted to, and transduce tumor cells, which are subsequently killed. However, it will be appreciated that the type of cell, which is targeted by the phage depends on the type of cell-targeting ligand expressed on the surface of the bacteriophage. In the Examples, tumor cells are used illustratively to show that the complex of the invention exhibit a significantly improved transduction.

Recombinant bacteriophages may include a variety of other functional elements in addition to the promoter, and the coding sequence encoding protein responsible for producing the therapeutic effect. Alternatively, the recombinant phage may be designed such that it integrates into the genome of a host cell. In this case, DNA sequences, which favour targeted integration (e.g. by homologous recombination) are envisaged. The bacteriophage may be used as a recombinant vector for the delivery of the transgene to a tissue specific target, irrespective of whether the vector is administered systemically or locally to a subject in vivo, applied to a mixture of cells in vitro, or applied to an organ ex vivo. In one embodiment of the invention, the nucleic acid may be DNA, which may lie genomic DNA or cDNA. Non-naturally occurring cDNA may be preferred in some embodiments. In another embodiment, the nucleic acid may be RNA, such as antisense RNA or shRNA.

As described in the Examples, the inventors investigated whether the multifunctional bacteriophage of the first aspect could be modified to further improve its gene transfer efficiency. The inventors realized that the major intracellular obstacle to a bacteriophage and transgene expression is its sequestration in the lysosomes of the host target cell, and so they developed a phage which displays a peptide on its pVIII major coat protein, which assists the phage to escape from endosomes in order to avoid its degradation in the lysosomes. They observed that when the bacteriophage displays an endosome escape peptide (EEP), it significantly improved the levels of transgene expression.

Therefore, preferably the foreign peptide which is displayed on the pVIII capsid major coat protein comprises an endosome escape peptide (EEP). The inventors believe that this is an important feature of the invention.

Therefore, according to a second aspect of the invention, there is provided a recombinant targeted bacteriophage for expressing a transgene in a target cell transduced with the bacteriophage, the bacteriophage comprising a nucleic acid sequence encoding at least one pVIII capsid major coat protein that is configured to display an endosome escape peptide (EEP) thereon, and a transgene which encodes a protein which exerts a biological effect on a target cell transduced by the bacteriophage.

Preferably, the bacteriophage of the second aspect comprises a nucleic acid sequence encoding a pIII capsid minor coat protein that is configured to display a cell-targeting ligand for enabling delivery of the bacteriophage to the target cell.

Endosome escape peptides (EEPs) are known for their potential to promote escape of vectors from endosomes by inducing disruption of endosomes (endosmolytic peptides) or by fusion with the endosomal membranes (fusogenic peptides). Accordingly, in one embodiment, the EEP is an endosmolytic peptide. In another embodiment, the EEP is a fusogenic peptide.

The inventors tested three different EEPs, the H5WYG peptide, the INF7 peptide, and the PC1 peptide. An embodiment of the sequence of the H5WYG peptide is: GLFHAIAHFIHGGWHGLIHGWYG [SEQ ID NO: 9]. An embodiment of the sequence of the INF7 peptide is: GLFEAIEGFIENGWEGMIDGWYG [SEQ ID NO: 10]. An embodiment of the sequence of the PC1 peptide is: HWYDSFVPWGHQ [SEQ ID NO: 11].

Hence, the endosome escape peptide may be selected from a group consisting of: the H5WYG peptide (SEQ ID No: 9), the INF7 peptide (SEQ ID No: 10), and the PC1. (SEQ ID No: ii) peptide, or a functional fragment or variant thereof. Preferably, the EEP is the H5WYG peptide or the PC1 peptide, or a functional fragment or variant thereof.

Preferably, the EEP is displayed on the recombinant pVIII capsid major coat protein. Hence, preferably the coding sequence of the EEP is fused in frame with the recombinant pVIII coding gene.

Hence, in a preferred embodiment, the bacteriophage of the first or second aspect comprises a first nucleic acid sequence encoding a pIII capsid minor coat protein that is configured to display a cell-targeting ligand for enabling delivery of the phage to a target cell, a second nucleic acid sequence encoding a wild type pVIII capsid major coat protein, a third nucleic acid sequence encoding a recombinant pVIII capsid major coat protein, wherein either or both of the major coat proteins is configured to display an EEP, and a transgene which encodes a protein which exerts a biological effect on the target cell.

The inventors also looked at the rate of transport of the bacteriophage of the invention to the nucleus, as they believed that this represents another rate-limiting step to transgene expression. As described in the Examples, the inventors found that when the bacteriophage displays a nuclear localization signal (NLS) peptide, it also surprisingly improved the levels of transgene expression.

Accordingly, preferably the foreign peptide which is displayed on the pVIII capsid major coat protein comprises a nuclear localization signal (NLS) peptide. The inventors believe that this is another important feature of the invention.

Hence, according to a third aspect of the invention, there is provided a recombinant targeted bacteriophage for expressing a transgene in a target cell transduced with the bacteriophage, the bacteriophage comprising a nucleic acid sequence encoding at least one pVIII capsid major coat protein that is configured to display a nuclear localization signal (NLS) peptide thereon, and a transgene which encodes a protein which exerts a biological effect on a target cell transduced by the bacteriophage.

Preferably, the bacteriophage of the third aspect comprises a nucleic acid sequence encoding a pIII capsid minor coat protein that is configured to display a cell-targeting ligand for enabling delivery of the bacteriophage to the target cell.

Nuclear localization signal peptides are known to the skilled person, and the inventors tested several of these, including the NLS peptide from the large tumour antigen of simian virus 40 (SV40 T antigen), optimized SV40 NLS, the optimized short M9 (osM9), and a heptamer NLS peptide.

An embodiment of the sequence of the SV40 NLS is: (PKKKRKV—[SEQ ID No: 12]). An embodiment of the sequence of optimized SV40 NLS is: (SSDDEATADAQHAAPPKKKRKV—[SEQ ID No:13]). An embodiment of the sequence of a non-classical NLS, optimized short M9 (osM9) is: YNNQSSNRGPYK—[SEQ ID No:14]. An embodiment of the sequence of the heptamer NLS peptide is: QPSPSPT—[SEQ ID No:15].

Hence, the NLS peptide may be selected from a group consisting of: the large tumour antigen of simian virus 40 (SV40 T antigen—SEQ ID No: 12); optimized SV40 NLS (SEQ ID No: 13); the optimized short M9 (osM9) (SEQ ID No: 14); and a heptamer NLS peptide (SEQ ID No: 15), or a functional fragment or variant thereof. Preferably, the NLS peptide is the large tumour antigen of simian virus 40 (SV40 T antigen), the optimized SV40 NLS or the optimized short M9 (osM9), or a functional fragment or variant thereof.

Preferably, the NLS peptide is displayed on the recombinant pVIII capsid major coat protein. Hence, preferably the coding sequence of the NLS peptide is fused in frame with the recombinant pVIII coding gene.

Hence, in another preferred embodiment, the bacteriophage of the first, second or third aspect comprises a first nucleic acid sequence encoding a pIII capsid minor coat protein that is configured to display a cell-targeting ligand for enabling delivery of the phage to a target cell, a second nucleic acid sequence encoding a wild type pVIII capsid major coat protein, a third nucleic acid sequence encoding a recombinant pVIII capsid major coat protein, wherein one of the major coat proteins is configured to display an EEP and the other major coat protein is configured to display an NLS peptide, and a transgene which encodes a protein which exerts a biological effect on the target cell.

As described in the Examples, the inventors have appreciated that the negative charge of the M13 bacteriophage surface plays a crucial role in the extracellular barriers to phage due to the generation of high non-specific binding to positively charged molecules (around 35% of proteins in the human proteome). The inventors have therefore used a genetic approach to change the negative N-term of the major wild type (wt) pVIII coat protein into a mixture of anionic and cationic terminal groups by introducing a short charged neutralizing peptide termed AKAS (Ala-Lys-Ala-Ser). They have found that the incorporation of the AKAS peptide into the coat protein resulted in neutralisation of the negative charge, and even resulted in a net positive charge on the phage.

Accordingly, preferably the wild type pVIII major coat protein of the bacteriophage of the first aspect comprises an N-terminal modification which neutralises the negative charge of the surface of the phage, and preferably results in a net positive charge at physiological pH. The modification preferably comprises a tetrapeptide comprising the amino acid sequence AKAS located in the N-terminal of the major coat wt pVIII protein, and preferably between residues Gly3 and Asp4 of the protein.

In a fourth aspect, there is provided the targeted bacteriophage according to the first, second or third aspect, for use in therapy or diagnosis.

The invention may be used for the treatment of a wide variety of diseases due to the target-specific nature and the improved transduction efficiency of the recombinant bacteriophage of the invention. Consequently, the therapeutic opportunities of recombinant bacteriophages used in gene therapy may be significantly increased by the invention due to (i) minimisation of any side-effects, which may occur due to off-target effects of the recombinant bacteriophage, and (ii) significantly improved target-specific cellular transduction. The invention may be used prophylactically to prevent disease, or after the development of a disease, to ameliorate/treat it.

Hence, in a fifth aspect, there is provided the targeted bacteriophage according to the first, second or third aspect, for use in a gene therapy technique.

In a sixth aspect, there is provided a method of treating, preventing or ameliorating a disease in a subject using a gene therapy technique, the method comprising administering, to a subject in need of such treatment, a therapeutically effective amount of the targeted bacteriophage according to the first aspect.

It will be appreciated that the invention may also be used to create a variety of different bacteriophages that can be used for the treatment and/or diagnosis of a variety of diseases depending on the nature of the recombinant bacteriophage and the displayed foreign proteins. For example, in an embodiment where the bacteriophage comprises a tumor-targeting ligand and/or which comprises a transgene expressing an anti-tumor protein (e.g. the HSVtk gene), then it may be used to treat cancer. Hence, the target cell in the gene therapy technique is preferably eukaryotic, and preferably mammalian.

The inventors have clearly demonstrated that the multifunctional bacteriophage of the invention exhibits elevated transgene expression in a transduced target cell. Hence, they believe that the phage will have a significant commercial value in the delivery of vaccines.

Thus, in a seventh aspect, there is provided a vaccine comprising the bacteriophage according to the first, second or third aspect.

In an eighth aspect, there is provided use of the bacteriophage according to the first, second or third aspect, for vaccine delivery.

The vaccine is preferably a DNA vaccine. The vaccine preferably comprises a suitable adjuvant. In an embodiment, the bacteriophage vector may be used to carry a transgene or DNA cassette encoding an antigen to stimulate the body's immune system. The multifunctional phage may also be used to directly display and express the antigen of interest on the major pVIII coat proteins, thus providing a unique platform for the simultaneous delivery, by a single phage particle, of numerous antigens as vaccine DNA vaccines or proteins readily expressed on the phage surface.

The inventors also believe that the bacteriophage of the invention can be used in a variety of different genetic-molecular imaging techniques, such as positron emission tomography (PET) or SPECT imaging.

Hence, in a ninth aspect there is provided use of the bacteriophage according to the first, second or third aspect, in a genetic-molecular imaging technique.

The transgene harboured by the phage may encode HSVtk and/or the sodium/iodide symporter (NIS), and the phage is preferably used in combination with a radiolabelled substrate. For example, the human sodium/iodide symporter (NIS) imaging gene is preferably used in combination with $I^{124}$ for clinically applicable positron emission tomography (PET) imaging, or with $I^{125}/^{99m}Tc$-pertechnetate for clinically applicable SPECT imaging.

Alternatively, the HSVtk gene is preferably used in combination with radiolabeled nucleoside analogues such as the 20-[18F]-fluoro-20-deoxy-1-b-D-arabino-furanosyl-5-ethy-luracil ([18F]FEAU).

It will be appreciated that the recombinant bacteriophages according to the invention (i.e. referred to hereinafter as "agent") may be used in a medicament which may be used in a monotherapy, or as an adjunct to, or in combination with, known therapies for treating, ameliorating, or preventing disease, such as cancer. The agents according to the invention may be combined in compositions having a number of different forms depending, in particular, on the manner in which the composition is to be used. Thus, for example, the composition may be in the form of a powder, tablet, capsule, liquid etc. or any other suitable form that may be administered to a person or animal in need of treatment. It will be appreciated that the vehicle of medicaments according to the invention should be one which is well-tolerated by the subject to whom it is given.

Medicaments comprising the agents according to the invention may be used in a number of ways. For instance, oral administration may be required, in which case the agents may be contained within a composition that may, for example, be ingested orally in the form of a tablet, capsule or liquid. Compositions comprising agents of the invention may be administered by inhalation (e.g. intranasally). Compositions may also be formulated for topical use. For instance, creams or ointments may be applied to the skin.

Agents according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (e.g. at least daily injection).

In a preferred embodiment, agents and compositions according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the agent that is required is determined by its biological activity and bioavailability, which in turn depends on the mode of administration, the physiochemical properties of the agent (i.e. bacteriophage), and whether it is being used as a monotherapy, or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the disease. Additional factors depending on the particular subject being treated will result in a need to adjust dosages, including subject age, weight, gender, diet, and time of administration.

Generally, a daily dose of between 0.01 µg/kg of body weight and 500 mg/kg of body weight of the agent according to the invention may be used. More preferably, the daily dose is between 0.01 mg/kg of body weight and 400 mg/kg of body weight, and more preferably between 0.1 mg/kg and 200 mg/kg body weight.

As discussed in the Examples, the agent may be administered before, during the or after the onset of disease. For example, the agent may be administered immediately after a subject has developed a disease. Daily doses may be given systemically as a single administration (e.g. a single daily injection). Alternatively, the agent may require administration twice or more times during a day. As an example, the agent may be administered as two (or more depending upon the severity of the disease being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses.

Known procedures, such as those conventionally employed by the pharmaceutical industry (e.g. in vivo experimentation, clinical trials, etc.), may be used to form specific formulations comprising the bacteriophage according to the invention and precise therapeutic regimes (such as daily doses of the agent and the frequency of administration).

Hence, in a tenth aspect of the invention, there is provided a pharmaceutical composition, comprising the bacteriophage according to the first, second or third aspect, and a pharmaceutically acceptable vehicle.

The composition can be used in the therapeutic amelioration, prevention or treatment of any disease in a subject that is treatable with gene therapy, such as cancer.

The invention also provides, in an eleventh aspect, a process for making the pharmaceutical composition according to the tenth aspect, the process comprising contacting a therapeutically effective amount of the bacteriophage according to the first, second or third aspect, and a pharmaceutically acceptable vehicle.

A "subject" may be a vertebrate, mammal, or domestic animal. Hence, agents, compositions and medicaments according to the invention may be used to treat any mammal, for example livestock (e.g. a horse), pets, or may be used in other veterinary applications. Most preferably, however, the subject is a human being.

A "therapeutically effective amount" of agent (i.e. bacteriophage) is any amount which, when administered to a subject, is the amount of drug that is needed to treat the target disease, or produce the desired effect, e.g. result in tumor killing.

For example, the therapeutically effective amount of agent used may be from about 0.01 mg to about 800 mg, and preferably from about 0.01 mg to about 500 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the recombinant bacteriophage) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The recombinant bacteriophage according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmoregulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The recombinant bacteriophage-polymer (hybrid) vector may be prepared as a sterile solid composition that may be dissolved or suspended at the time of administration using sterile water, saline, or other appropriate sterile injectable medium.

The recombinant bacteriophage and pharmaceutical compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The recombinant bacteriophage according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/polynucleotide/polypeptide sequence", "functional variant" and "functional fragment", can be a sequence that has at least 40% sequence identity with the amino acid/polynucleotide/polypeptide sequences of any one of the sequences referred to herein, for example 40% identity with the gene identified as SEQ ID No.1, 3 or 7 (which encode one embodiment of wild-type pVIII, recombinant pVIII and pIII, respectively), or 40% identity with the polypeptide identified as SEQ ID NO.2, 4 or 8 (i.e. one embodiment of wild-type pVIII, recombinant pVIII and pIII, respectively).

Amino acid/polynucleotide/polypeptide sequences with a sequence identity which is greater than 65%, more preferably greater than 70%, even more preferably greater than 75%, and still more preferably greater than 80% sequence identity to any of the sequences referred to is also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:— (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=-1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as $(N/T)*100$, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:— Sequence Identity=$(N/T)*100$.

Alternative methods for identifying similar sequences will be known to those skilled in the art. For example, a substantially similar nucleotide sequence will be encoded by a sequence which hybridizes to the sequences shown in SEQ ID Nos. 1, 3 or 7, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No's. 2, 4, 8-15.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline; and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

Figure 3:
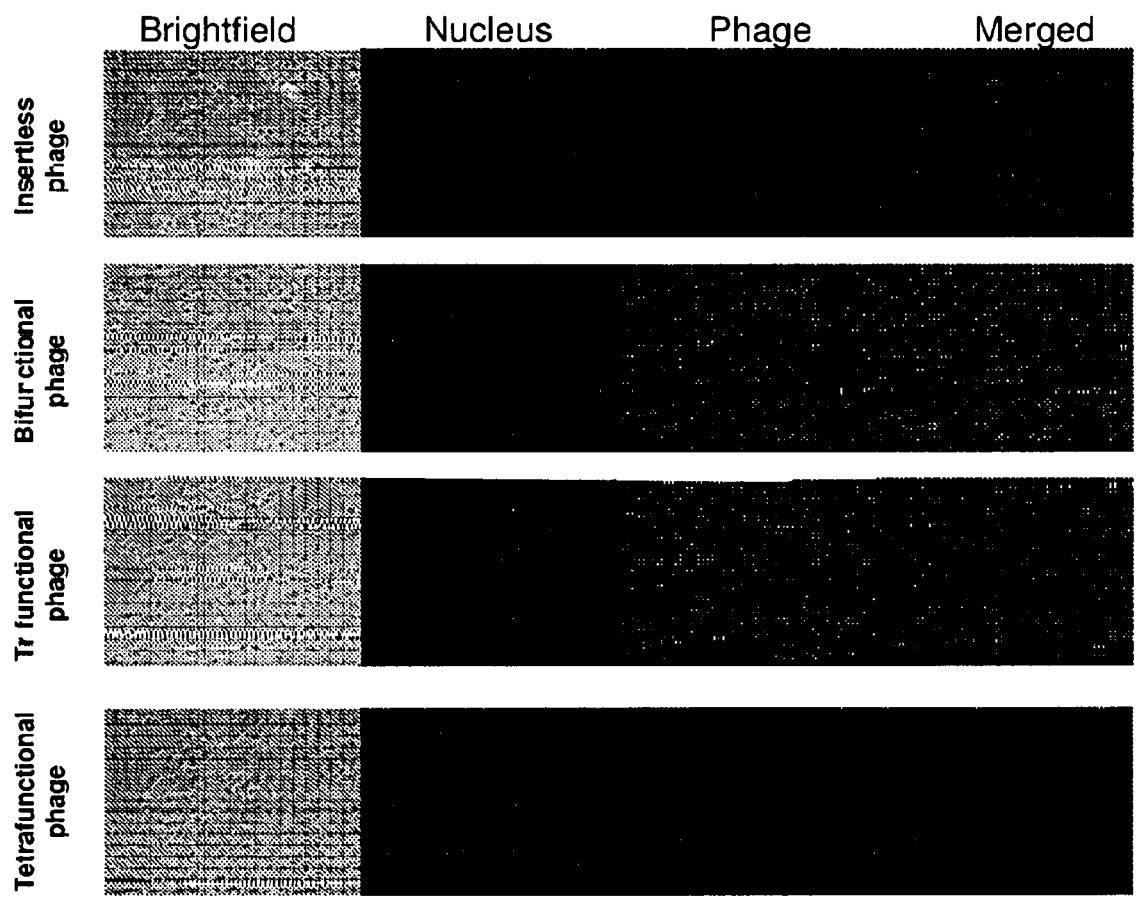
Figure 4:
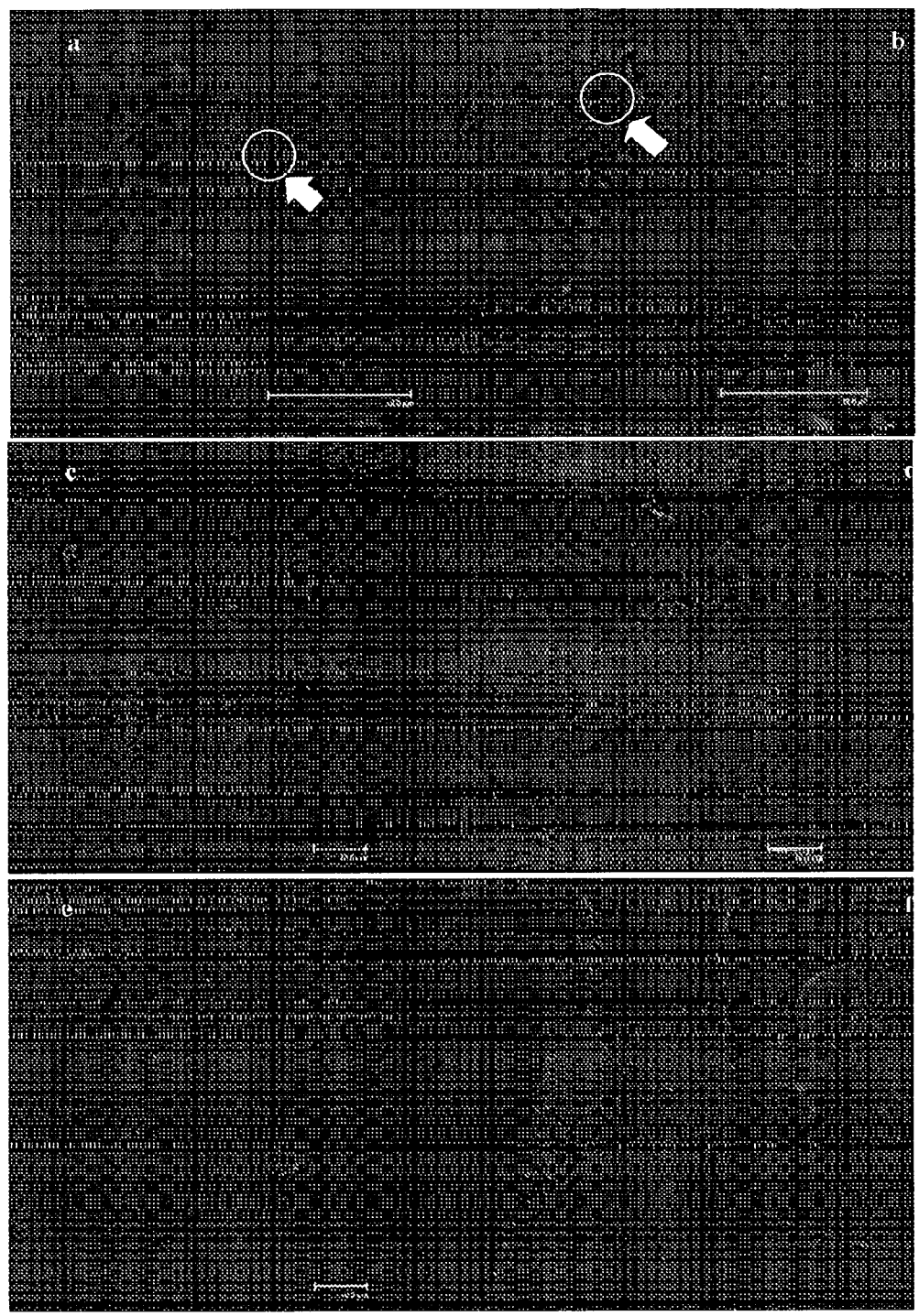
Figure 5:
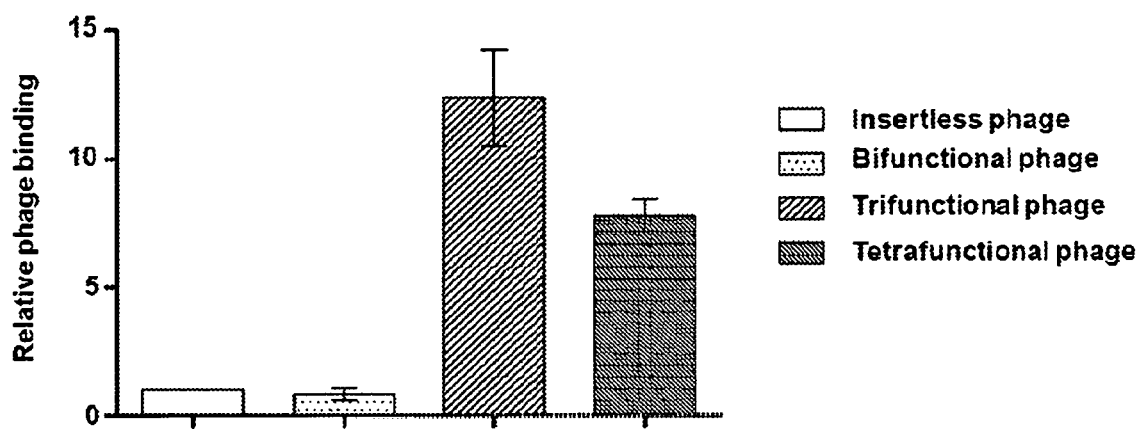
Figure 6:
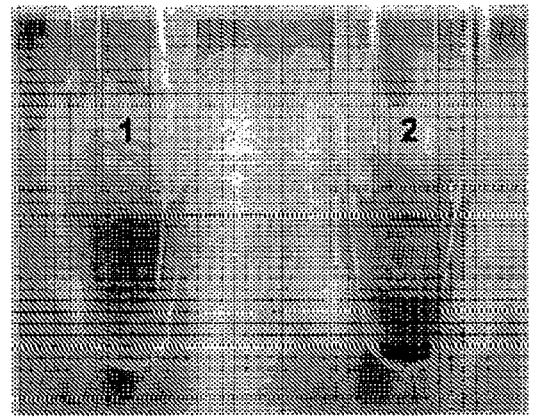
Figure 6:
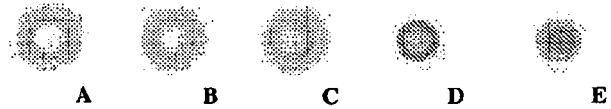
Figure 7:
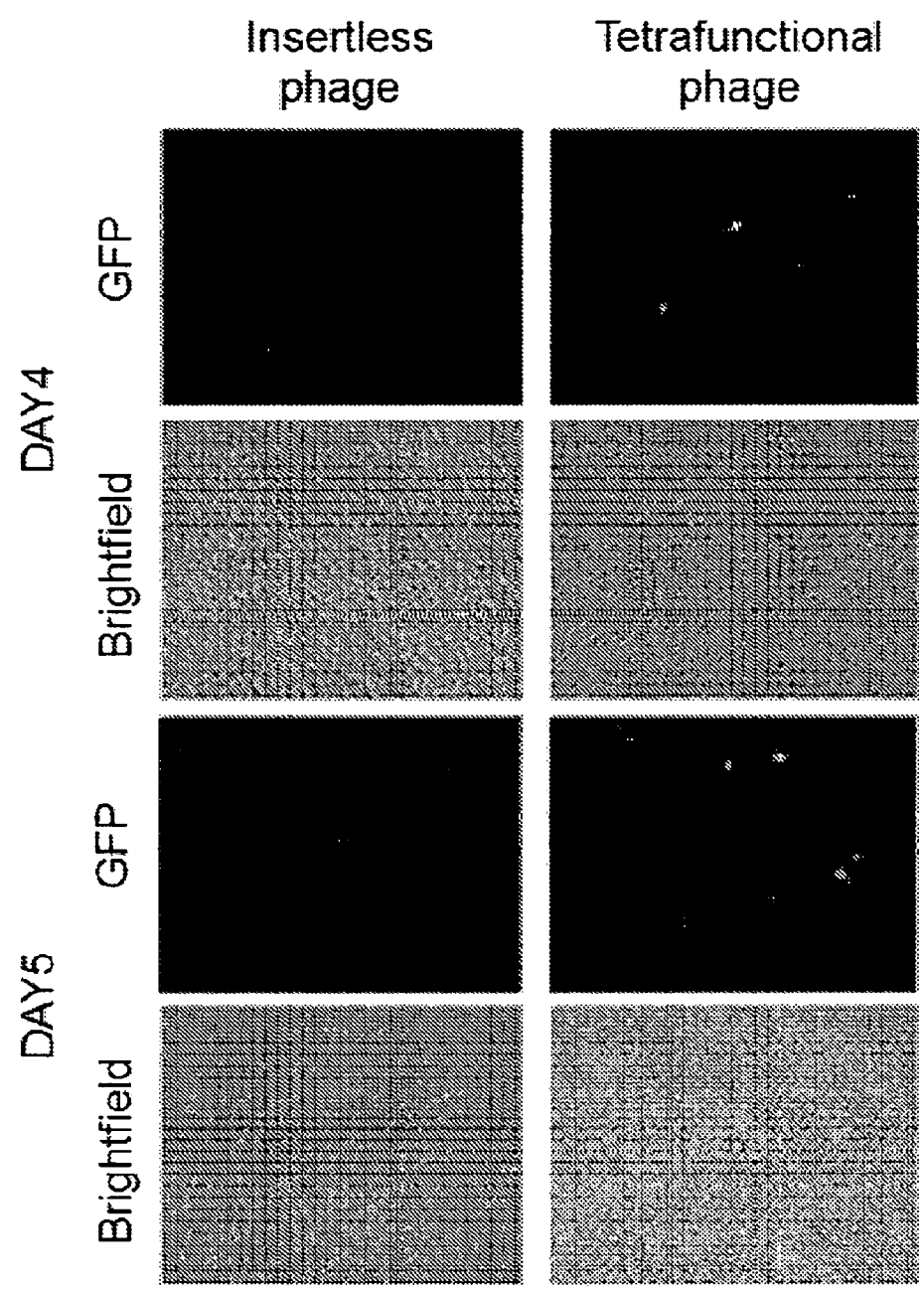
Figure 8A:
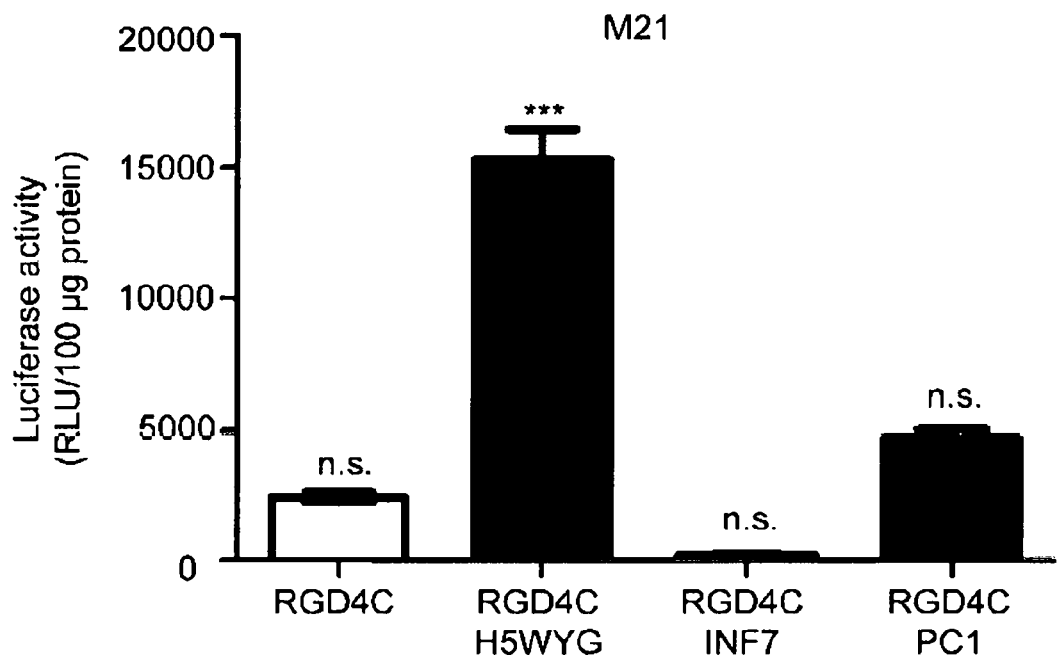
Figure 8B:
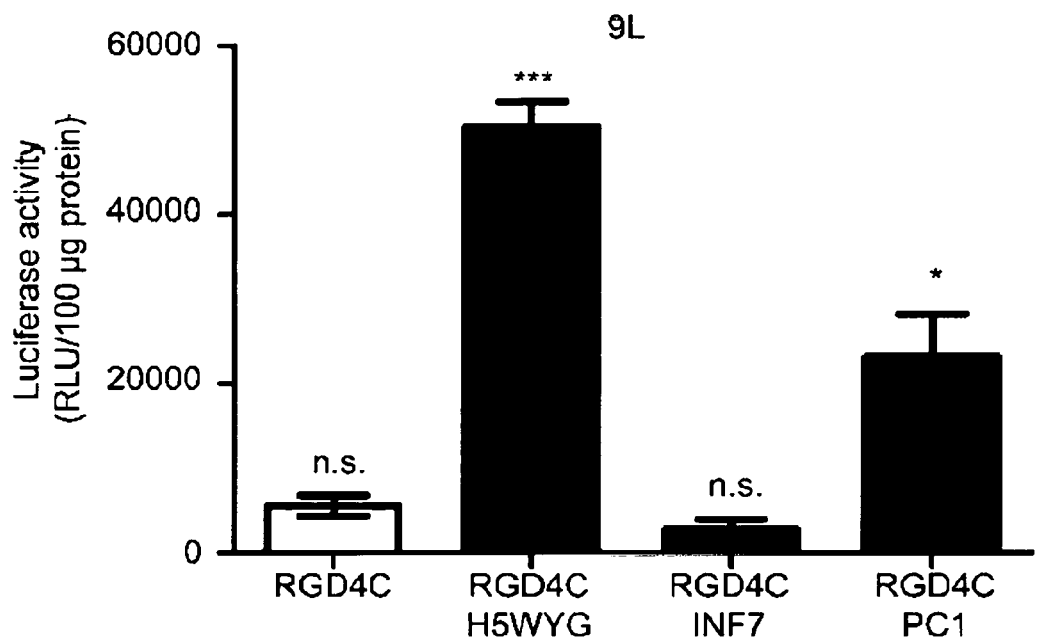
Figure 9A:
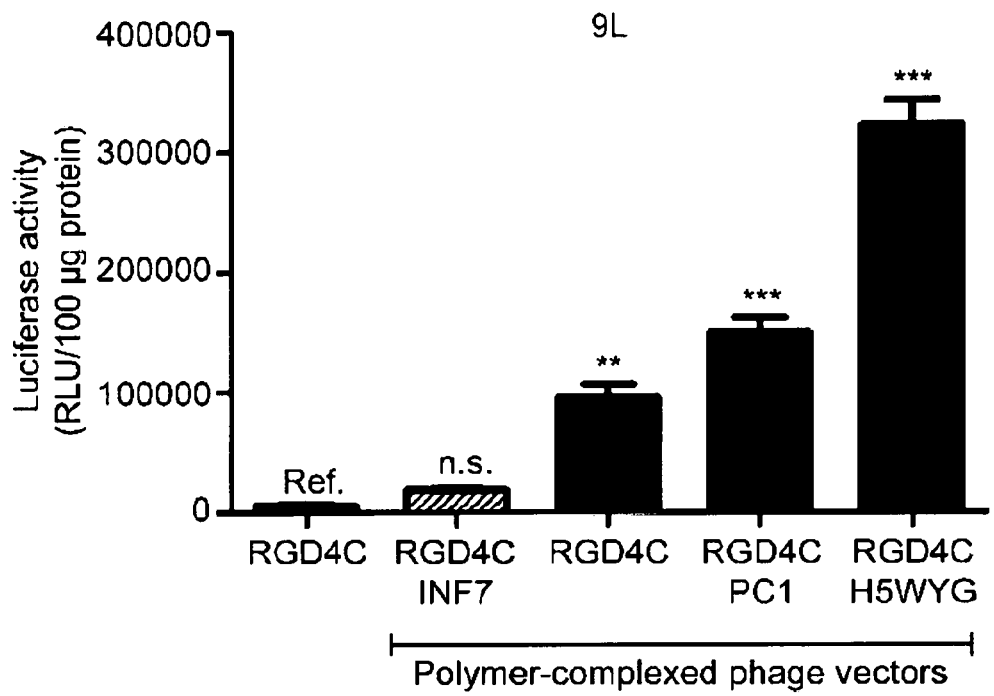
Figure 9B:
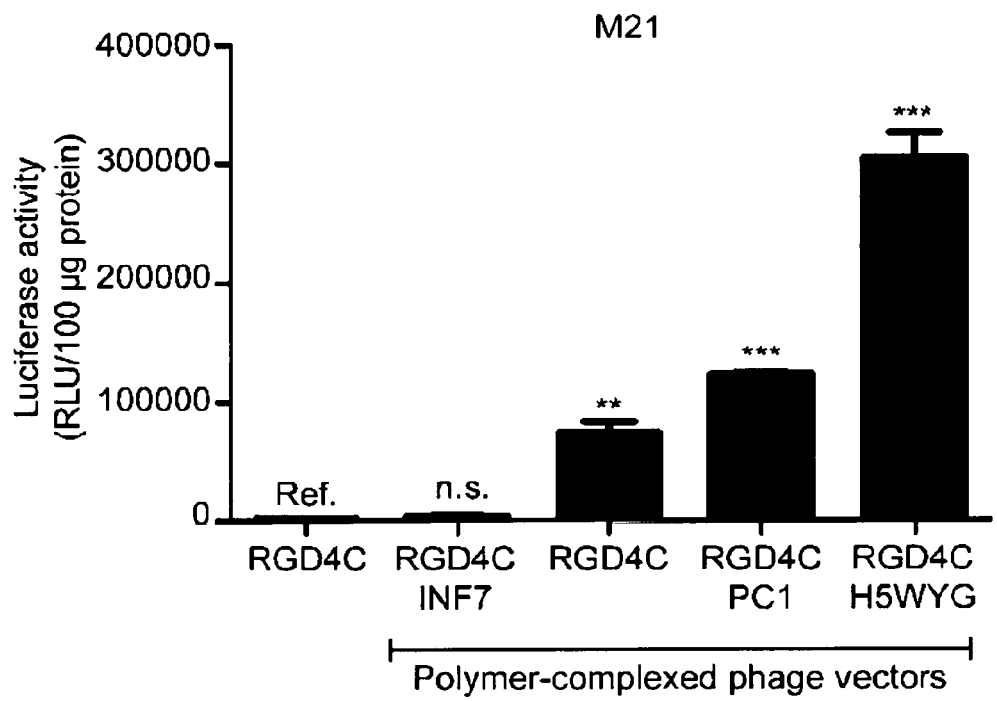
Figure 10:
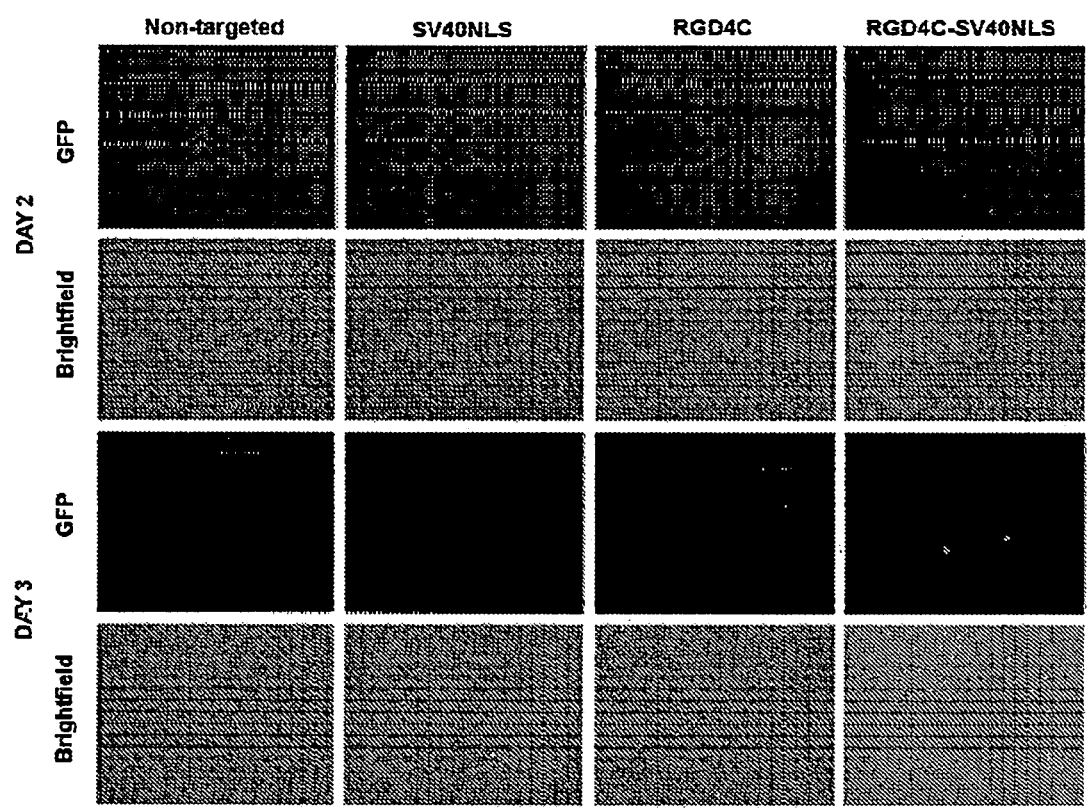
Figure 11:
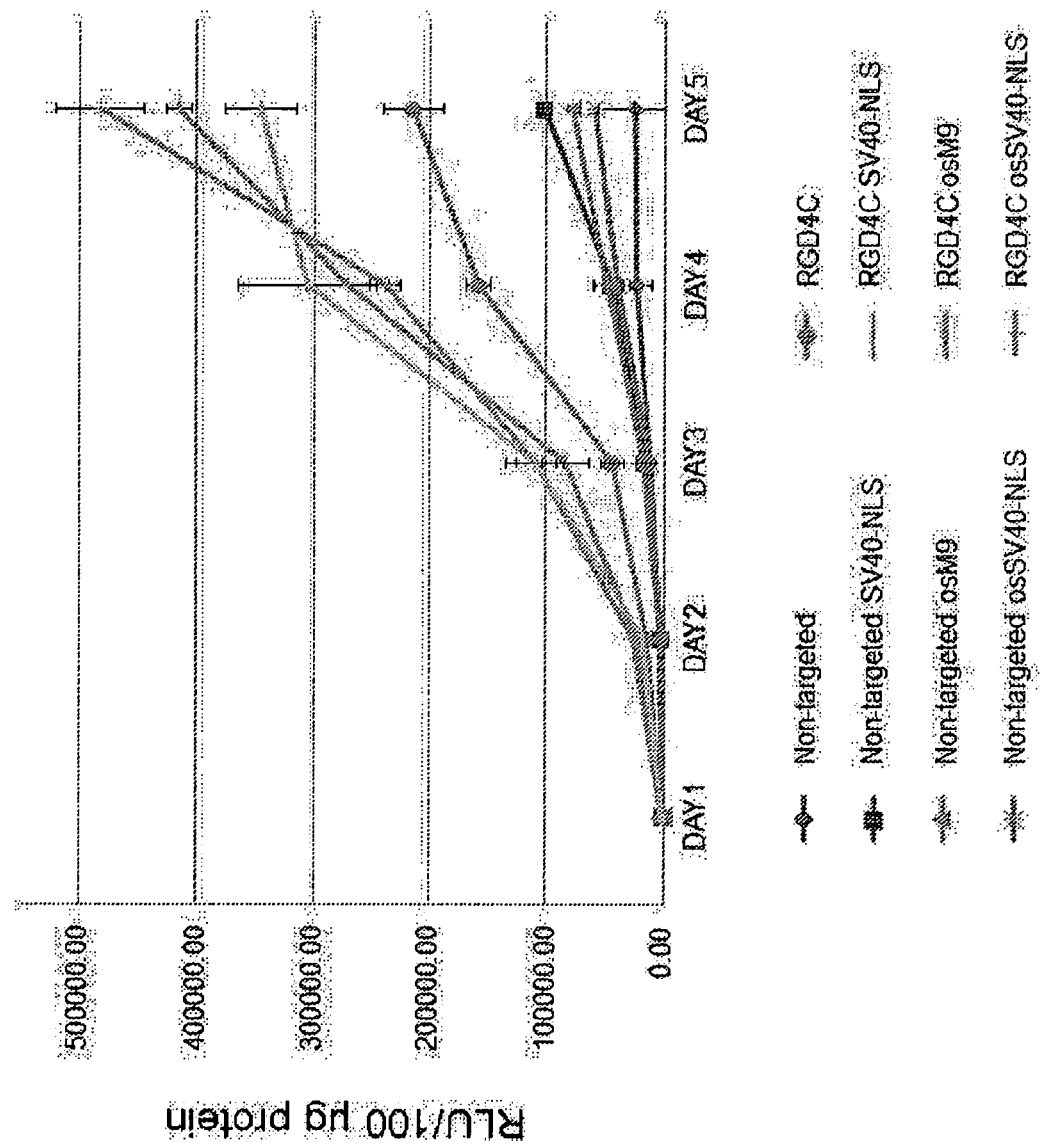
Figure 13:
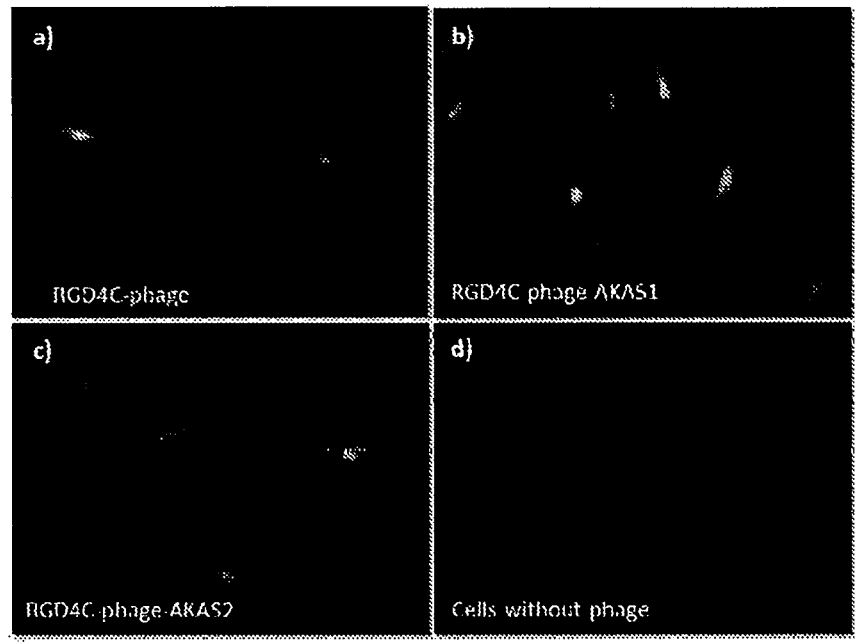
Figure 13:
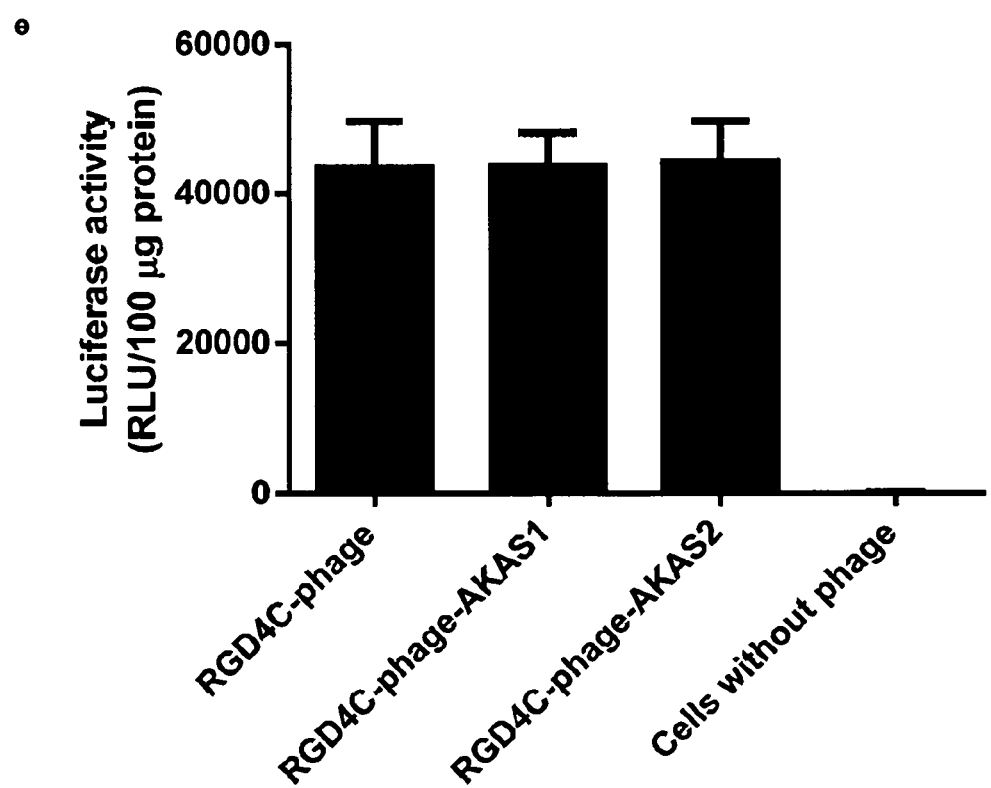
Figure 14:
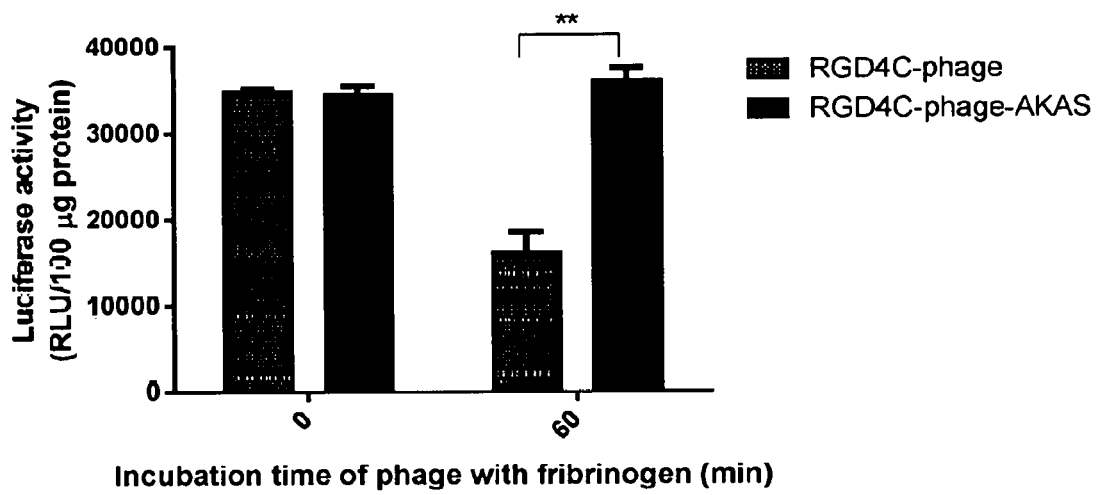
Figure 15:
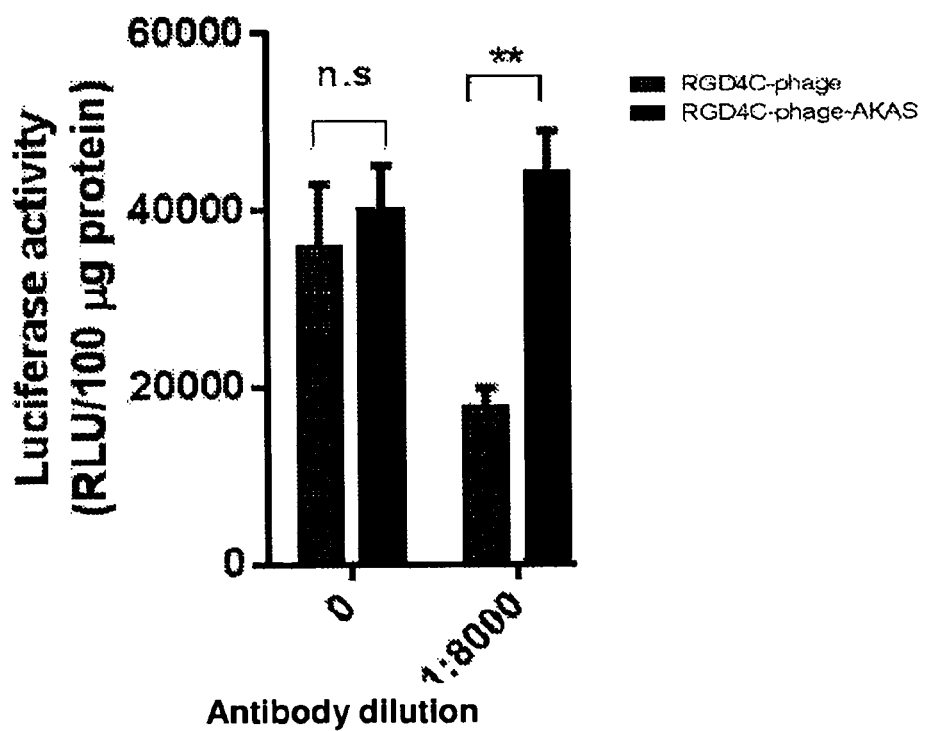

FIG. 1 is a schematic representation of an embodiment of a multifunctional phage particle model system according to the invention. In the embodiment shown the phage is tetrafunctional displaying a targeting RGD4C ligand on the pIII minor coat protein and multiple copies of gold binding peptide and streptavidin-binding peptide on the surface. A mammalian transgene cassette, driven by the cytomegalovirus promoter (CMV), was also inserted in the bacteriophage genome to allow transgene expression by the multifunctional phage;

FIG. 2 is a schematic representation of four phage vectors used in this study. a) Insertless phage, without any ligand. b) bifunctional phage, displaying the RGD4C ligand and carrying a mammalian transgene cassette. c) Trifunctional phage, simultaneously carrying RGD4C, a streptavidin-binding peptide and a transgene cassette. d) Tetrafunctional phage, simultaneously displaying RGD4C, streptavidin-binding peptide, gold-binding peptide and transgene cassette;

FIG. 3 shows immunofluorescence-based phage binding and internalization assay with cultured human M21 melanoma cells. The red colour represents fluorescence related to phage staining, and the blue colour shows fluorescence of DAPI-stained cell nuclei. Cells were incubated with different phage preparations, all carrying a phage input of $1.0 \times 10^6$ transducing units (TU/cell);

FIG. 4 shows confocal microscopy images. Shown are M21 melanoma cells incubated with phage preparations (input of $1 \times 10^6$ TU/cell) and labelled with anti-bacteriophage antibody (red) and DAPI nucleus stain (blue). a) free phage, b) internalizing phage, c) control insertless phage, d) bifunctional phage, e) trifunctional phage, tetrafunctional phage (Scale bar, 10 μm);

FIG. 5 shows that the tetrafunctional phage of the invention binds to streptavidin. Different phage constructs were incubated with immobilised streptavidin and washed prior to infection of K91. Binding of the trifunctional and tetrafunctional phage, both of which display streptavidin-binding peptides, were proved by the greater number of bacterial transducing units. Shown are the mean±SEM from triplicate wells;

FIG. 6 shows binding of the tetrafunctional phage to gold nanoparticles. a) Precipitation assay showing precipitate formation upon mixing a gold colloidal solution with the tetrafunctional phage. b) Dots A, B, and C represent insertless phage, bifunctional and trifunctional phage, respectively. Significant staining was observed in dots D and E representing the tetrafunctional phage;

FIG. 7 shows GFP expression by the multifunctional phage in HEK293 cells. GFP expression, analyzed by three independent observers, was detected at all time-points post cell treatment. Shown are representative images of cells at days 4 and 5 following transduction with the multifunctional phage;

FIGS. 8*a* and 8*b* show multifunctional phage carrying endosome-escape-peptides boosts transgene expression from phage. Human M21 melanoma cells or rat 9L glioma cells were treated with $3 \times 10^4$ TU/cell of targeted RGD4C multifunctional phage expressing the reporter Luciferase gene and displaying the endosome-escape-peptides H5WYG, INF or PC1. Luciferase transgene expression by vectors in cells was evaluated by measurement of the luciferase activity at day 3 post vector transduction. Luciferase activity was expressed as the mean relative luminescence units (RLU) normalized to protein amount;

FIGS. 9*a* and 9*b* show multifunctional phage carrying endosome-escape-peptides and cationic polymers remarkably boosts transgene expression from phage. Human M21 melanoma cells or rat 9L glioma cells were treated with $3 \times 10^4$ TU/cell of targeted RGD4C multifunctional phage expressing the reporter Luciferase gene, displaying the endosome-escape-peptides H5WYG, INF or PC1 and complexed with cationic polymers. Luciferase transgene expression by vectors in cells was evaluated by measurement of the luciferase activity at day 3 post vector transduction. Luciferase activity was expressed as the mean relative luminescence units (RLU) normalized to protein amount;

FIG. 10 shows GFP expression in HEK293 cells at days 2 and 3 post-transduction. Analysis of GFP expression in HEK293 cells showed that transgene expression from phage vectors simultaneously displaying RGD4C and SV40-NLS ligands was detectable at 48 hours, whereas GFP expression from the phage displaying RGD4C ligand only started at 72 hours post vector transduction;

FIG. 11 shows time course of phage-mediated Luc transgene expression. HEK293 cells were seeded in 48-well plates and grown until 70-80% confluence. The cells were then incubated for 4 hours with $1 \times 10^6$ TU/cell of different phage displaying RGD4C and different nuclear localization signal compared to cells treated with non-targeted vectors. The luciferase assay was performed over a time course of 5 days after vector transduction. The results represent the average RLU of targeted per 100 μg protein of triplicate wells+/−the standard error of the mean (S.E.M);

FIG. 12 shows AKAS display does not affect the phage titre and results in new physical characteristics. a) Bacterial colonies after infection of E. coli K91Kan with $2 \cdot 10^{-7}$ dilution of the parental multifunctional RGD4C-phage and the two new phages (RGD4C-phage-AKAS1 and RGD4C-phage-AKAS2). b, c) Phages were incubated overnight with the cationic DEAE-dextran polymer. The suspension containing the phage particles not attached to the polymer was recuperated and used to infect E. coli K91Kan. b) LB-agar plates (containing 40 μg/ml Tet and 100 μg/ml Kan) showing differential colony formation between the RGD4C and the two AKAS phages. One representative plate of each phage and each dilution is shown. c) Phage recovery in terms of percentage of input. These assays were repeated twice in triplicate and the results shown are representative of one experiment. Statistical analysis: One way ANOVA (a and c). * p<0.05; n.s=no significant;

FIG. 13 shows 9L rat glioblastoma cells are transduced by parental and the two new AKAS phages carrying the GFP or Luc reporter genes. The 9L cells (60-80% confluent in 48-well plates) were incubated with $3 \times 10^4$ TU/cell (containing the GFP or Luc reporter gene) for 4 h in serum-free medium. After 4 h, complete medium was added. GFP expression was monitored at day 5 post phage transduction with a) RGD4C-phage and (b and c) the two clones of the new phage RGD4C-phage-AKAS1/2. As negative control we used d) cells without phage treatment. All pictures represent a portion of one of the triplicate wells. e) The quantitative Luc measurement assay was performed at day 3 post phage transduction and normalized to protein concentration determined by the Bradford assay. Results represent the average±SEM relative luminescence units (RLU)/100 μg of protein from triplicate wells. All assays were repeated twice;

FIG. 14 shows Luciferase expression after incubation of phage with fibrinogen. The 9L cells (60-80% confluent in 48-well plates) were transduced with $3 \times 10^4$ TU/cell containing the Luc reporter gene for 4 h in serum free media. Two conditions were assessed: cells treated directly with the phages (left bars) or cells treated with phage after 60 minutes incubation with fibrinogen (right bars). After 4 h, complete medium was added. Results represent the average±SEM relative luminescence units (RLU)/100 μg of protein from triplicates at day 3 post-transduction. The experiment was repeated twice. p<0.01; and FIG. 15 shows the effect of anti-phage antibody on luciferase expression in cells transduced with RGD4C-phage or RGD4C-phage-AKAS. The 9L cells (60-80% confluent in 48-well plates) were incubated with $3 \times 10^4$ TU/cell solution containing complete media and several anti-phage antibody concentrations. Results represent the average±SEM relative luminescence units (RLU)/100 μg of protein from triplicates at day 3 post-transduction and the same experiment was repeated twice. Statistical analysis: T-student test.  p<0.01; n.s=no significant.

EXAMPLES

Summary

The inventors investigated the barriers to gene transfer by bacteriophage in eukaryotic cells. First they searched for the existence of extracellular barriers to phage and found that one of the limitations in phage is its surface negative charge which hinders phage accessibility to the negatively charged eukaryotic cell membranes and subsequent binding to the target cell receptor. In addition, the inventors assessed the intracellular trafficking of phage in mammalian cells and found that, after internalization, the major intracellular obstacle to bacteriophage gene transfer efficiency is phage sequestration in acidic endosomal vesicles, and its subsequent degradation in the lysosomal compartment. Accordingly, the inventors developed strategies to overcome both of these extracellular and intracellular barriers to phage-mediated transgene expression. Compared with eukaryotic viral vectors, bacteriophage requires additional commands to by-pass these extracellular and intracellular obstacles. One strategy adopted was to transfer, into the phage capsid, the efficient mechanisms developed and used by many eukaryotic viruses. For example, to attain endosomal release, one strategy was to integrate, into the phage capsid, histidine-rich peptides to buffer against the ATP-dependent proton pump located in the membrane of endosomes resulting in endosomal disruption and subsequent viral escape.

As shown in FIGS. 1 and 2, as a proof-of-concept, the inventors used the known RGD4C-phage displaying the targeting ligand, for mammalian receptor binding, on the pIII minor coat protein because it is well-characterized. The pIII has the advantage of displaying large targeting ligands since chimeric pIII molecules which contain large inserts appear to package into phage well. As the pIII minor coat protein displays the targeting ligand CDCRGDCFC (RGD4C), the inventors aimed at displaying the peptides for overcoming mammalian cell barriers on the pVIII major coat protein. Since insertion of large peptides inserts on the major coat protein by itself cannot support phage assembly, the inventor created a RGD4C-phage genome that bears two genes which encode different types of pVIII molecule. The first pVIII protein is the initial integral wild-type protein, which is used to display of a second functional peptide, and the other pVIII protein is the recombinant pVIII that served to display large sized peptides. The recombinant pVIII was removed from the f88-4 phage and inserted into the targeted RGD4C-phage, and then expressed from an IPTG-inducible tac promoter. Thus, the coat of the new multifunctional phage (bearing the two pVIII coat proteins) was composed of both wild-type and recombinant pVIII subunits; the latter typically comprises at least ~150 of the 3900 subunits of the wild-type, which can vary depending on the concentration of the IPTG (at least 1 mM) used to induce the tac promoter and subsequently the expression of the recombinant pVIII.

Materials and Methods

Construction of the Multifunctional Bacteriophage

Targeted multifunctional phage particles were made in a multiple-step process. First, a targeting ligand peptide of choice (e.g. RGD4C) was displayed on the pIII minor coat protein to generate a targeted backbone phage vector for binding to a mammalian cell receptor. Second, a DNA fragment containing a recombinant rpVIII gene was inserted in the genome of the targeted phage, followed by display of the peptide ligand of interest. Third, a peptide of interest was displayed on the wild-type pVIII major coat protein by site-directed mutagenesis. Finally, a mammalian transgene cassette was inserted in an intergenomic region of the phage genome.

Expression of the targeting ligand on the phage's capsid was performed by using the M13-derived fUSE5 phage plasmid (accession number AF218364). Targeting peptides were displayed on the pIII minor coat protein of the fUSE5 phage as previously described in the detailed protocol (Hajitou, A. et al. Design and construction of targeted AAVP vectors for mammalian cell transduction. *Nat Protoc* 2, 523-531 (2007)) by cloning the corresponding oligonucleotide sequences flanked by BglI restrictions sites into the SfiI site of the pIII coat gene of a targeted RGD4C-fUSE5 phage.

Design and Construction of the RGD4C-Phage Containing Two Major Coat Proteins

The f88-4 phage (GenBank Accession AF218363) whose total genome length is 9234 base-pairs harbours two genes encoding two different types of the major coat protein, pVIII. One pVIII is recombinant (rpVIII) and the other is wild-type (wt pVIII). Hence, the f88-4 coat is composed of both wild-type and recombinant pVIII subunits. To create a targeted RGD4C-phage bearing an additional recombinant pVIII coat protein, the inventors used the BamHI and XbaI restriction enzymes to digest the plasmid DNA of the two existing phage RGD4C-fUSE5 and f88-4, because they have unique restriction sites present at similar locations in the DNA backbone of the two phages. Then, fragments with the corresponding cassettes (3925 bp fragment containing RGD4C from RGD4C-fUSE5 plasmid and a 5360 bp fragment containing the recombinant pVIII from f88-4 plasmid) were ligated to create a chimeric RGD4C-phage construct in which pIII and recombinant pVIII were mapped to their locations. A control non-targeted chimera phage (fUSE5/f88-4) without a targeting ligand RGD4C was also constructed.

Insert Preparation and Cloning of Peptides in the Recombinant pVIII of RGD4C-fUSE5/f88 Phage To display a peptide on the recombinant rpVIII coat protein, the corresponding oligonucleotide sequence and its complementary oligonucleotide were designed (see Table 1).

TABLE 1

Oligonucleotide (oligo) sequences for peptide display on the recombinant rpVIII coat protein. The sense and anti-sense oligos are 5' phosphorylated and the nucleotides X correspond to the sequence encoding for the peptide ligand of interest

| Primer | Sequence (5'-3') |
| --- | --- |
| Sense oligo | 5'AGCTTTGCCAACGTXXXXXXXXXXXXXXXXXXXXCCTGCA-3' [SEQ ID No. 16] |
| Anti-sense oligo | 5'-GGXXXXXXXXXXXXXXXXXXXXXXXGACGTTGGCAA-3'[SEQ ID No. 17] |

The phosphorylated primers were mixed (20 pmol/primer), heated to 95° C. for 5 min and gradually cooled at room temperature to allow annealing. Annealing of sense and anti-sense oligonucleotides generated the HindIII and PstI sticky ends ready to ligate into the HindIII and PstI of the digested RGD4C-phage chimera plasmid. All general procedures employed for construction, production and analysis of recombinant phage, DNA sequencing, are detailed in previously published protocols (Petrenko V A and Brigati J R. In Emon JMV (ed.). 2007. Immunoassay and other Bioanalytical Techniques. CRC press, Taylor & Francis Group, Boca Raton, Fla.).

Display of Peptides on the Wild Type (wt) pVIII Major Coat Protein

Peptides of short length (up to 10 amino acid residues) were inserted into the major wt pVIII coat protein by using the Phusion Site-Directed Mutagenesis Kit (Thermo SCIENTIFIC). Briefly, synthetic oligonucleotide primers for mutagenic PCR were designed (see Table 2).

TABLE 2

Primer sequences used in site-directed mutagenesis. Both primers are 5' phosphorylated to avoid a spontaneous recircularization of the vector. Nucleotides in red (X) correspond to the peptide of interest.

| Primer | Sequence (5'-3') |
| --- | --- |
| Forward | P.XXXXXXXXXGATCCCGCAAAAGCGGCCTTTG [SEQ ID No. 18] |
| Reverse | P.AGCAGCGAAAGACAGCATCG [SEQ ID No. 19] |

A PCR (50 µL reaction) with Phusion Hot Start II DNA polymerase using double-stranded RGD-phage vector DNA as template and the forward/reverse primer pair was prepared and thermocycled using the following setup: 98° C. for 30 s, followed by 25 cycles at 98° C. for 15 s, 61° C. for 30 s and 72° C. for 5 min (approximately 30 s elongation per 500 bp). The linear PCR product was circularized by ligation using the Quick T4 DNA Ligase in a 5 minute reaction. Ligated DNA was transformed by heat shock into chemically competent DH5α E. coli bacteria, plated on Luria-Bertani broth (LB)-tetracycline (Tet) agar plates and incubated for 24 h at 37° C. Single colonies were picked and grown overnight in 5 mL LB-Tet. DNA was isolated by using a QIAprep Spin Miniprep kit (QIAGEN) and sent to sequence (Macrogen).

Insertion of a Mammalian Transgene Cassette into the RGD4C-fUSE5/f88-4 Expression Vector To generate a targeted multifunctional phage particle for gene expression in mammalian cells, a eukaryotic transgene cassette was inserted into the SacI site located at 5650 bp in an intergenomic region of the phage genome. In brief, both the transgene cassette flanked by SacI restriction sites and the phage genome were digested with the Sac I restriction enzyme, then ligated. The phage DNA was subjected to SacI endonuclease digestion (3 h at 37° C.), dephosphorylation (1 hr at 37° C.) and SacI inactivation (30 min at 70° C.). The vector band (90.8 kb) was purified by agarose gel electrophoresis (QIAgen gel extraction kit) and ligated with the transgene cassette expressing a transgene. Quick T4 DNA Ligase was used for a 5 minute ligation reaction. Following transformation of bacteria with the ligation product, colonies were picked and DNA isolation was performed. To check which plasmids contained the insert, isolated DNA was run at 1% ethidium bromide containing agarose gel (in 1×TAE [40 mM Tris (sigma), 20 mM acetic acid (Sigma) and 1 mM Ethylenediaminetetraacetic acid (EDTA, Sigma)] at 90 V for 1 hour. Ladder (Fermentas) was used as an indicator of molecular weight). Midiprep (QIAGEN) instead of miniprep (QIAGEN) was performed because of the low copy plasmid obtained with vectors that contained the transgene cassette.

Expression of Nuclear Localisation Signal (NLS)

The phage vector RGD4C-fUSE5/f88.4 (GenBank Accession for fUSE5 is AF218364, for f88-4 AF218363) is composed of recombinant gene III containing RGD4C-encoding inserts and recombinant gene VIII that was used as the scaffold for nuclear targeting ligand (NLS) display. Oligonucleotides encoding the desired NLS were then inserted. Next, the mammalian transgene cassette was inserted in the genome of this chimeric phage.

Foreign inserts encoding NLS peptide were spliced between the HindIII and PstI cloning sites after removing the stuffer that lies between them in the vector. Productive inserts had the following general structure:

```
5'-AGC|TTT|GCC|NNN|...|NNT|GCA-3'

3'-AA|CGG|NNN|...|NN-5'
```

NLS peptides that were used included:—

1. The Classical SV40 NLS (PKKKRKV—[SEQ ID No:12])
2. The optimized SV40 NLS (SSDDEATADAQHAAPP-KKKRKV—[SEQ ID No:13]),
3. A nonclassical NLS, the optimized short M9 (osM9); YNNQSSNRGPYK—[SEQ ID No:14]
4. A heptamer peptide (QPSPSPT—[SEQ ID No:15]).

The sequence of the sense oligonucleotide used to produce the Classical SV40 NLS peptide is:

[SEQ ID No. 16]
5' AGCTTTGCCAACGTCCCGAAAAAAAAACGCAAAGTGCCTGCA 3'

The sequence of the antisense oligonucleotide used to produce the Classical SV40 NLS peptide is:

[SEQ ID No. 17]
5' GGCACTTTGCGTTTTTTTTTCGGGACGTTGGCAA 3'

The sequence of the sense oligonucleotide used to produce the optimized SV40 NLS peptide is:

[SEQ ID No. 18]
5' AGCTTTGCCAACGTCAGCAGCGATGATGAAGCGACCGCGGATAGCCA

GCACGCGGCGCCGCCGAAAAAAAAACGCAAAGTGCCTGCA 3'

The sequence of the antisense oligonucleotide used to produce the optimized SV40 NLS peptide is:

[SEQ ID No. 19]
5' GGCACTTTGCGTTTTTTTTTCGGCGGCGCCGCGTGCTGGCTATCCGC

GGTCGCTTCATCATCGCTGCTGACGTTGGCAA 3'

The sequence of the sense oligonucleotide used to produce the optimized short M9 (osM9) NLS peptide is:

[SEQ ID No. 20]
5' AGCTTTGCCAACGTCTATAACAACCAGAGCAGCAACCGCGGCCCGTA

TAAACCTGCA 3'

The sequence of the antisense oligonucleotide used to produce the optimized short M9 (osM9) NLS peptide is:

[SEQ ID No. 21]
5' GGTTTATACGGGCCGCGGTTGCTGCTCTGGTTGTTATAGACGTTGG

CAA 3'

The sequence of the sense oligonucleotide used to produce the heptamer peptide NLS peptide is:

[SEQ ID No. 22]
5' AGCTTTGCCAACGTCCAGCCGAGCCCGAGCCCGACCCCTGCA 3'

The sequence of the antisense oligonucleotide used to produce the heptamer peptide NLS peptide is:

[SEQ ID No. 23]
5' GGGGTCGGGCTCGGGCTCGGCTGGACGTTGGCAA 3'

Expression of Endosome-Escape Peptide (EEP)

The phage vector RGD4C-fUSE5/f88.4 (GenBank Accession for fUSE5 is AF218364, for f88-4 AF218363) plasmid is composed of recombinant gene III containing RGD4C-encoding inserts and recombinant gene VIII and was used as the scaffold for endosome escape peptide (EEP) display. Oligonucleotides encoding the desired EEP were then inserted. Next, the mammalian transgene cassette was inserted in the genome of this chimeric phage.

Three different EEP's were used:—

1. The H5WYG peptide which is a synthetic histidylated fusogenic peptide with endosomal buffering capacity, derived from the N-terminal sequence of the HA2 sunbunit of the influenza virus hemagglutinin (Midoux, P., Kichler, A., Boutin, V., Maurizot, J. C. & Monsigny, M. Membrane permeabilization and efficient gene transfer by a peptide containing several histidines. *Bioconjug Chem* 9, 260-267 (1998).

The sequence of the H5WYG peptide is:

[SEQ ID NO: 9]
GLFHAIAHFIHGGWHGLIHGWYG.

The sequence of the sense oligonucleotide used to produce the H5WYG peptide is:

[SEQ ID NO: 24]
5' AGCTTTGCCAACGTCGGCCTGTTCCATGCGATCGCGCATTTCATCCA

TGGCGGCTGGCATGGCCTGATCCATGGCTGGTATGGCCCTGCA 3'

The sequence of the antisense oligonucleotide used to produce the H5WYG peptide is:

[SEQ ID NO: 25]
5' GGGCCATACCAGCCATGGATCAGGCCATGCCAGCCGCCATGGATGAAA

TGCGCGATCGCATGGAACAGGCCGACGTTGGCA 3'

2. The INF7 peptide is a pH-dependent fusogenic peptide derived from the N-terminal of influenza HA2. INF7 (a 23-mer acidic derivative) in particular was shown to have high specificity for low pH (5.5), and yielded higher membrane lytic activity (Plank, C., Oberhauser, B., Mechtler, K., Koch, C. & Wagner, E. The influence of endosome-disruptive peptides on gene transfer using synthetic virus-like gene transfer systems. *J Biol Chem* 269, 12918-12924 (1994).

The sequence of the INF7 peptide is: GLFEAIEGFIEN-GWEGMIDGWYG [SEQ ID NO:10].

The sequence of the sense oligonucleotide used to produce the INF7 peptide is:

[SEQ ID NO: 26]
5' AGCTTTGCCAACGTCGGCCTGTTCGAAGCGATCGAAGGCTTCATCGA

AAACGGCTGGGAAGGCATGATCGATGGCTGGTATGGCCCTGCA 3'

The sequence of the antisense oligonucleotide used to produce the INF7 peptide is: 5'

[SEQ ID NO: 27]
GGGCCATACCAGCCATCGATCATGCCTTCCCAGCCGTTTTCGATGAAGCC

TTCGATCGCTTCGAACAGGCCGACGTTGGCAA 3'

3. The PC1 peptide is a pH-dependent endosomolytic peptide identified by phage display. Due to its tryptophan content, it was alleged that the peptide could cause endosomal membrane lysis by insertion into lipidic bilayers Hirosue, S. and Weber, T. (2006). pH-Dependent lytic peptides discovered by phage display. *Biochemistry*. 45 (20): 6476-6487.

The sequence of the PC1 peptide is:

[SEQ ID NO: 11]
HWYDSFVPWGHQ.

The sequence of the sense oligonucleotide used to produce the PC1 peptide is:

[SEQ ID NO: 28]
5' AGCTTTGCCAACGTCCATTGGTATGATAGCTTCGTGCCGTGGGGCCA

TCAGCCTGCA 3'

The sequence of the antisense oligonucleotide used to produce the PC1 peptide is:

[SEQ ID NO: 29]
5' GGCTGATGGCCCCACGGCACGAAGCTATCATACCAATGGACGTTGGC AA 3'

Phage Production, Purification and Titration

Targeted and control phage vectors are amplified, isolated and purified from the culture supernatant of host bacteria (*E. coli* K91Kan) as the inventors recently reported in detail in Hajitou, A. et al. Design and construction of targeted AAVP vectors for mammalian cell transduction. *Nat Protoc* 2, 523-531 (2007). Vector particles in suspension are sterile-filtered through 0.45-μm filters. Because the recombinant gene pVIII in the chimera RGD4C-phage was transcribed from an IPTG-inducible tac promoter, the inventors added 1 mM of IPTG (Isopropyl β-D-1-thiogalactopyranoside) during phage production to display the peptide inserts.

(i) Phage Production

*E. coli* K91Kan was used to produce the phages because they are pilus-positive F+ bacteria and can therefore be infected by the newly produced phage particles during the overnight growth. This phenomenon resulted in higher titers. Briefly, *E. coli* K91Kan were grown in a 7 ml Terrific Broth (TB), containing 100 μg/mL Kanamycin at 37° C. by shaking at 250 rpm until a log-phase growth was obtained (1 hour). One ml of the mixture was then incubated 1 hour at room temperature with 50 μL of *E. coli* DH5α culture carrying the desired phage vector. The next step was to mix the previously incubated 1 mL with 15 mL of LB containing 40 μg/ml tetracycline and 100 μg/ml Kanamycin and incubated for 4 hours at 37° C. This was then transferred to 500 mL LB broth (40 μg/ml tetracycline and 100 μg/ml kanamycin) and incubated overnight at 37° C.

(ii) Phage Purification

Bacterial growth cultures were centrifuged for 30 min at 6000 g and 4° C. to pellet the bacteria. The supernatant was collected and incubated with 15% Polyethylene-glycol/Sodium chloride (PEG/NaCl, Sigma) and kept on ice for 2 hours to allow precipitation of the phage viral particles. The suspension was centrifuged for 30 min at 10000 g and 4° C. to get the white phage pellet. The supernatant was discarded and centrifuged for an additional 5 min. The pellet was suspended in 7 ml 1× Phosphate-Buffered Saline (PBS, sigma) with shaking during 1 hour at 37° C. Again, PEG/NaCl (15% of the mixture volume) was added and kept on ice for 2 hours. After incubation, centrifugation for 30 min at 14000 g and 4° C. was carried out and, afterwards, the supernatant was discarded. The pellet was then re-suspended in 500 μl of 1×PBS and agitated at 37° C. until a homogeneous suspension was obtained (approximately 1 h and 30 min). The mixture was transferred to an eppendorf tube and centrifuge using a benchtop centrifuge for 10 min at 13000 rpm for 10 min (repeated 2-3 times) to remove any residual bacteria debris and finally sterile-filtered through a 0.45 μm filter.

(iii) Phage Titration

The amount of phage viral particles in suspension were sterile-filtered through 0.45-μm filters, then titrated by infection of host *E. coli* K91 Kan bacteria for colony counting and expressed as bacterial transducing units (TU) as reported in the detailed protocol (Hajitou, A. et al. *Nat Protoc* 2, 523-531 (2007).

Infectivity Assay

To check whether the display of the tetrapeptide AKAS on the wt pVIII affects the phage ability to infect bacteria, the inventors performed an infectivity assay. The parental multifunctional phage and the newly produced AKAS multifunctional phage were adjusted to the identical titre and submitted to serial dilutions, then 5 μL of each dilution were incubated with 1 ml of *E. coli* K91Kan for 20 min at room temperature. After incubation, 200 μL of the dilutions $5 \times 10^{-6}$, $5 \times 10^{-7}$ and $5 \times 10^{-8}$ were spread in triplicates on LB agar plates containing 40 μg/ml tetracycline and 100 μg/ml kanamycin and incubated overnight at 37° C. Finally, the colonies at $5 \cdot 10^{-7}$ and $5 \cdot 10^{-8}$ dilutions were counted.

Cell Targeting and Fluorescent Imaging

Cells were seeded on 18 mm² coverslips in 12-well plates. The next day, cells at approximately 50-60% confluence were incubated with phage for 4 hours at 37° C. Cells were washed and fixed with phosphate buffered saline (PBS) containing 4% paraformaldehyde. Cells were then incubated for 5 minutes 50 mM Ammonium Chloride to quench free aldehyde groups from fixation, permeabilized with 0.2% Triton X-100, washed, and blocked with PBS containing 2% BSA, and the cells were incubated with rabbit anti-M13 bacteriophage antibody for 1 hr at room temperature followed by a 1 hr incubation with Cy3-labeled anti-rabbit IgG antibody. Finally, cells were mounted in the presence of DAPI. Images were acquired with either an Olympus fluorescence microscope and a Zeiss LSM510 laser scanning confocal microscope.

Mammalian Cell Transduction by Phage

A subconfluent monolayer culture of cells was seeded in 48-well plates and incubated at 37° C. for 24 hours, until 80% confluent. Phage/serum-free medium mixture was incubated with cells at 37° C. with a ratio of $1 \times 10^6$ TU phage per cell or otherwise, as stated in the text. When mixed with cationic polymers, phage was used at $3 \times 10^4$ TU/cell, while the cationic polymers poly-D-lysine (PDL), or diethylaminoethyl-dextran DEAE.DEX) were applied at 7 μg/ml and 15 μg/ml, respectively. After 4 hours of incubation, complete medium was added to each well. The plate was incubated in $CO_2$ incubator at 37° C. and the medium was renewed every day. Transgene expression was assessed at various time points depending on the experiment carried out. For Luciferase assay, the Promega Steady-Glo® luciferase assay kit was used to evaluate the expression of Luciferase reporter transgene in phage-transduced cells. Luciferase expression WAS quantified using a Turner Biosystems microplate luminometer. Luciferase assays were performed in triplicate and normalized to 100 µg cell protein, as determined by the Bradford assay.

DEAE-Dextran Polymer Assay

To coat the plate surface, 1 ml of DEAE-dextran 2 mg/ml (sigma) was incubated overnight at 37° C. The excess of polymer was removed and washed once with 1 ml 1× PBS before addition of 5 µL of phage in 1 ml PBS and incubated overnight at 37° C. The phage suspension was recovered and used to infect *E. coli* K91 Kan following the same steps described in the infectivity assay.

Anti-Phage Antibody Assay

Cells were treated as described above and transduced with a mixture of phage and an anti-phage polyclonal antibody (Sigma). The Antibody was used at 1:8000 dilution and cell transduction was determined and evaluated by the Luciferase assay.

Fibrinogen Assay

Wells of the 48 wells-plate were coated with fibrinogen 2 mg/ml (Sigma) during 2 hours at 37° C. The excess of fibrinogen was removed and 5 µL of phage in 110 µL serum free media were added. After 1 hour incubation at 37° C. cell transduction was performed as described in the cell transduction section. The levels of transduction were determined by Luciferase assay.

Results

Example 1—Construction and Characterization of the Multifunctional Phage Display Model System The RGD4C-phage is an M13-derived fUSE5 phage (GenBank Accession number: AF218364) that bears a single gene pVIII; while the M13-derived f88.4 phage (GenBank Accession number: AF218363) bears two genes pVIII, encoding two different types of pVIII molecules namely wild-type and the recombinant pVIII. Thus, a fragment containing the recombinant pVIII gene under a tac promoter, was removed from the f88.4 phage and inserted into an intergenomic region of the RGD4C-phage to generate an RGD4C-phage bearing the two pVIII genes. Next, the inventors inserted a mammalian transgene cassette in the genome of this multifunctional phage. To show that display of peptides, on the pVIII major coat proteins, remain intact and functional in the context of the multifunctional phage, and as proof of principle, the inventors constructed phage displaying the two well characterized peptides, i.e. (i) a streptavidin-binding peptide, and (ii) a gold-binding peptide (FIGS. 1 and 2). The coding sequences of the streptavidin-binding peptide (ANRLCHPQFPCTSHE—[SEQ ID No:5]) were fused in frame with recombinant pVIII coding gene (Chen, L. et al. Design and validation of a bifunctional ligand display system for receptor targeting. Chem Biol 11, 1081-1091 (2004). The coding sequence of a gold-binding peptide (VSGSSPDS—[SEQ ID No:6]) (Huang, Y. et al. Programmable assembly of nanoarchitectures using genetically engineered viruses. *Nano Lett* 5, 1429-1434 (2005)), was displayed on the wild-type major coat protein wt pVIII. Thus, the resulting phage particle simultaneously displayed RGD4C ligand at the phage end and multiple copies of gold binding peptide and streptavidin-binding peptide on the surface, in addition to harbouring the mammalian transgene cassette in its genome. Sequencing analyses were carried out to confirm the presence of the correct sequences and orientation of inserts and the mammalian transgene cassette, and to determine if any mutations occurred during cloning.

Example 2—Cell-Surface Integrin Binding Characteristics of the Multifunctional Phage After demonstrating that all peptides are correctly displayed on the pIII minor coat protein as well as on the recombinant and wild type pVIII major coat proteins of the multifunctional phage, the inventors sought to confirm that the moieties carried by the multifunctional phage remain intact and functional. Firstly, to validate the function of the RGD4C targeting ligand, displayed on the pIII minor coat protein, the inventors assessed binding and receptor-mediated entry of the multifunctional phage to cells expressing the $\alpha_v\beta_3$ integrin receptors for RGD4C. Immunofluorescence-staining assays and confocal microscopy with antibodies against the phage capsid were carried out on the M21 human melanoma cells because they express high levels of $\alpha_v\beta_3$ integrin (Albelda, S. M. et al. Integrin distribution in malignant melanoma: association of the beta 3 subunit with tumor progression. *Cancer Res* 50, 6757-6764 (1990). The inventors showed that the targeting and receptor-mediated internalization capabilities of the RGD4C peptide remained intact within the tetrafunctional phage relative to those observed for the trifunctional and bifunctional phages. Negative controls showed only background signal (FIGS. 3 and 4)

Example 3—Testing the Streptavidin Binding Capacity of the Multifunctional Phage To test that the streptavidin-binding peptide was functional when displayed on the capsid of the multifunctional phage, the inventors assessed the ability of this phage to bind to streptavidin in in vitro phage binding assays. Bound phages were recovered from streptavidin-coated plates by infection of host bacteria *E. coli* K91. Interestingly, the tetrafunctional and trifunctional phage, displaying a streptavidin-binding peptide, showed high and similar levels of binding to immobilized streptavidin. While, insertless phage (no RGD4C) and bifunctional RGD4C phage did not show any binding (FIG. 5).

Example 4—Testing the Gold Nanoparticles Binding Capacity of the Tetrafunctional Phage First, the inventors carried out a precipitation test. The phage solutions were mixed with a gold colloidal suspension (FIG. 6). After incubation, the mixtures of the insertless, bifunctional and trifunctional phage with the gold colloidal suspension remained clear (FIG. 6), whereas a visible precipitate was observed in the mixture with the tetrafunctional phage, indicating that gold colloids formed aggregates (FIG. 6).

Finally, to show functionality of the gold binding peptide displayed on the surface of multifunctional phage and its ability to bind to gold nanoparticles, the inventors carried out a dot blot-diffusion assay. Different phages were directly added onto the nitrocellulose membrane (FIG. 6). Subsequently, gold nanoparticles were added on top of phages dotted on the membrane. The gold binding capacity of phage can be determined by the diffusion pattern formation of gold nanoparticle on the membrane. Significant staining was observed in dots D and E, indicating that the tetrafunctional phage displaying gold-binding peptide could effectively bind gold nanoparticles (FIG. 6). In contrast, no staining was observed in control dots A (insertless phage), B (bifunctional) and C (trifunctional), where gold nanoparticles tend to move from the region of high concentration of phage to the surrounding regions of lower concentration of gold nanoparticles (FIG. 6), indicating that gold did not bind the insertless, bifunctional, and trifunctional, all of which lack the gold-binding peptide on the surface.

Example 5—Evaluation of Gene Expression by the Multifunctional Phage

To examine that the multifunctional phage can express transgenes in mammalian cells, the inventors conducted cell transduction experiments on the normal immortalized Human Embryonic Kidney HEK293 cell line. HEK293 cells have previously been used as a standard in vitro model for transduction by the RGD4C-phage as they express high levels of $α_vβ_3$ integrin receptor. In their first set of experiments, the inventors used vectors carrying the green fluorescent protein (GFP) reporter transgene. This reporter gene provides a convenient way to visualize expression of the transgene. Analysis of GFP expression showed GFP expression in cells by the multifunctional phage (FIG. 7). These data prove that the multifunctional phage mediates transgene expression in mammalian cells.

Example 6—Application of the Multifunctional Phage in Promoting Gene Transfer to Mammalian Cells by Phage Next, to investigate whether the multifunctional phage can be used to enhance phage applications, the inventors assessed the effect on gene transfer efficiency of phage. Since the inventors reported that the major intracellular obstacle to phage is its sequestration in the lysosomes, the inventors constructed as proof of concept, multifunctional phage displaying peptides to assist the phage to escape from endosomes in order to avoid its degradation in the lysosomes. Therefore, the inventor displayed on the recombinant pVIII coat protein of the multifunctional phage a panel of endosome-escape-peptides (EEPs) known for their potential to promote escape of vectors from endosomes by inducing disruption of endosomes (endosmolytic peptides) or by fusion with the endosomal membranes (fusogenic peptides). One approach tested was to transfer to the capsid on the multifunctional phage strategies already used by eukaryotic viruses to escape the endosomes. Three different EEPs were tested, the H5WYG peptide, the INF7 peptide, and the PC1 peptide. As initial cellular model to assess gene transfer efficacy, the inventors performed experiments in the M21 human melanoma cells and used phage carrying the Luciferase reporter gene.

The results show that the targeted multifunctional phage displaying the H5WYG peptide (RGD4C H5WYG) achieved substantial increase of gene transfer by phage compared to the original RGD4C-phage. The multifunctional phage displaying the PC1 peptide also showed significant increase of the phage gene transfer efficacy, while INF7 peptide had little effect as compared to the wild type RGD4C-phage (FIG. 8). To rule out the possibility that the observed effects are cell or species specific, the inventors repeated these experiments on the rat 9L glioma cells, known to express the $α_vβ_3$ receptor, and found a pattern of gene transfer efficacy by the multifunctional similar to that on the M21 cells. These data confirm that gene transfer efficacy of phage is markedly improved in the context of a multifunctional phage able to overcome the major mammalian intracellular barrier to gene transfer by phage.

Example 7—Overcoming Both Extracellular and Intracellular Major Obstacles to Phage, by a Single Multifunctional Bacteriophage. Promotes Gene Transfer by Phage Remarkably After demonstrating that gene transfer efficacy by phage can be dramatically increased by overcoming the major intracellular obstacle of phage degradation in the lysosomes, the inventors sought to use a multifunctional phage which overcomes both extracellular (cell accessibility) and intracellular (lysosomal degradation) major limitations of phage in one single particle. Thus, the multifunctional phage displaying the EEPs was mixed with cationic polymers (poly-D-lysine [PDL], or diethylaminoethyl-dextran [DE-AE.DEX]), to form multifunctional phage/polymer complexes. Here again, the inventors used phage carrying the luciferase reporter gene to assess gene transfer efficacy on both M21 and 9L cells. Firstly, the complexes of RGD4C-phage and cationic polymers showed significant enhancement of transgene expression by the phage compared to the uncomplexed phage (FIG. 9). Surprisingly, combination of both cationic polymer and the PC1 endosome-escape-peptide has further improved gene transfer by phage compared to phage/polymer (FIG. 9). However, and remarkably, combination of cationic polymer and the H5WYG peptide resulted in an exceptional increase of the gene transfer efficacy by phage in both M21 and 9L cells compared to all other combinations (FIG. 9). Indeed, the multifunctional phage combining the cationic polymer PDL and the H5WYG peptide showed ~100-fold increase of the reporter Luciferase expression in both M21 and 9L cells compared to the original RGD4C-phage that eradicated aggressive natural and sizeable (13 cm) tumours in a phage gene therapy trial in pet dogs (Paoloni M, Tandle A, Mazcko C, Hanna E, Kachala S, LeBlanc A, Newman S, Vail D, Henry C, Thamm D, Sorenmo K, Hajitou A, Pasqualini R, Arap W, Khanna C and Libutti S. 2009. Launching a novel preclinical infrastructure: comparative oncology trials consortium directed therapeutic targeting of TNF-α to cancer vasculature. PLoS One 4, e4972).

Example 8—Overcoming the Nuclear Transport Obstacle to Bacteriophage by the Multifunctional Phage Promotes its Gene Transfer Efficacy Transport to the nucleus represents another rate-limiting step to phage. Several eukaryotic viruses have developed successful strategies to target their genetic material to the nucleus. The inventors displayed on the phage capsid the nuclear localization signal (NLS) from animal viruses. Thus, to increase phage transport to the nucleus and subsequently the efficacy of transgene expression, the inventors generated a multifunctional phage that displays the targeting RGD4C ligand on the pIII minor coat protein and the NLS peptide, from the large tumour antigen of simian virus 40 (SV40 T antigen), on the recombinant major pVIII coat protein. Next, the inventors inserted the mammalian transgene cassette in the genome of this multifunctional phage. To examine transduction efficiency of the newly generated phage vector, the inventors compared the multifunctional phage displaying RGD4C ligand and SV40-NLS peptides to phage displaying RGD4C without the SV40-NLS peptide. The non-targeted phage displaying SV40-NLS only and phage without any ligands served as negative controls for mammalian cell transduction. As an in vitro model, the inventors used the normal immortalized HEK293 cell line. HEK293 cells have previously been used as a standard in vitro model for transduction by RGD4C-phage as they express high levels of $\alpha_v\beta_3$ integrin receptor of the RGD4C ligand. In their first set of experiments, the inventors used phage vectors carrying the GFP reporter transgene. Analysis of GFP expression in HEK293 cells showed that transgene expression from phage vector simultaneously displaying the NLS peptide and the targeting RGD4C ligand was detectable at 48 hours (FIG. 10), whereas GFP expression from the phage displaying only RGD4C ligand started later on at 72 hours post vector transduction consistently with previous reports. These data indicate that display of the NLS peptide on the pVIII coat protein of vector resulted in an early initiation of transgene expression. Also, GFP analyses overtime by three independent observers revealed a more pronounced GFP expression overtime in cells transduced with the targeted phage vector displaying the SV40-NLS (FIG. 10).

Next, after demonstrating the proof of efficacy with the SV40-NLS, the inventors sought to opt for the most suitable NLS that can achieve superior mammalian cell transduction by phage. The inventors screened a number of optimized NLS peptides, including the optimized osSV40-NLS from SV40 (SSDDEATADAQHAAPPKKKRKV—[SEQ ID No:13]) and the optimized short M9 (osM9, YNNQSSN-RGPYK—[SEQ ID No:14]). The classical SV40NLS (QPSPSPT—[SEQ ID NO:12]) was also included in these experiments. The inventors displayed all these NLS on the rpVIII of multifunctional phage vector carrying the Luc reporter transgene. Expression in HEK293 cells was monitored over a time course of 5 days after vector transduction. Transgene expression from each construct was evaluated in triplicates and luciferase activity was determined as the average relative luminescent units (RLU) per 100 µg protein as shown in FIG. 11. The inventors found that luciferase expression was significantly higher at all time-points post vector treatment (days 1 to 5) with all multifunctional phage simultaneously displaying either classical SV40-NLS, optimized osSV40-NLS or osM9 and RGD4C ligand compared to the multifunctional phage displaying RGD4C ligand only (FIG. 11).

Example 9—Construction of a Novel Multifunctional RGD4C-Phage Vector Containing a Wild Type Major Coat pVIII Protein with an Altered Charge The negative charge of the M13 bacteriophage surface plays a crucial role in the extracellular barriers to phage due to the generation of high non-specific binding to positively charged molecules (around 35% of proteins in the human proteome). The inventors have previously attempted to reduce this non-specific binding by using cationic polymers such as the DEAE-dextran to neutralize or convert to positive the negative surface of the virus. Herein, the inventors used the multifunctional phage to apply a genetic approach consisting of changing the negative N-term of the major wild type (wt) pVIII coat protein into a mixture of anionic and cationic terminal groups by introducing a short charged neutralizing peptide termed AKAS (Ala-Lys-Ala-Ser). Thus, the inventors generated a novel targeted multifunctional phage vector, termed RGD4C-phage-AKAS, with a new wt pVIII that has a modification at the N-terminal to neutralize the negative charge of the phage surface.

To engineer this new multifunctional phage, the first genetic engineering step was to introduce the tetrapeptide AKAS between residues Gly3 and Asp4 of the N-term of the major coat wt pVIII protein using the strategy of site-directed mutagenesis. After the successful PCR amplification of the vector the inventors analyzed 10 DH5α E. coli transformed colonies and all of them were RGD4C-phage-AKAS construct positive. The correct insertion of the AKAS nucleotide sequence was checked by sequencing. Second the inventors inserted a transgene cassette into the Sac-I site of the multifunctional phage as reported above. Finally, two positive multifunctional phage clones displaying the AKAS peptide were selected for the phage production and purification (see materials and methods section).

Figure 12A:
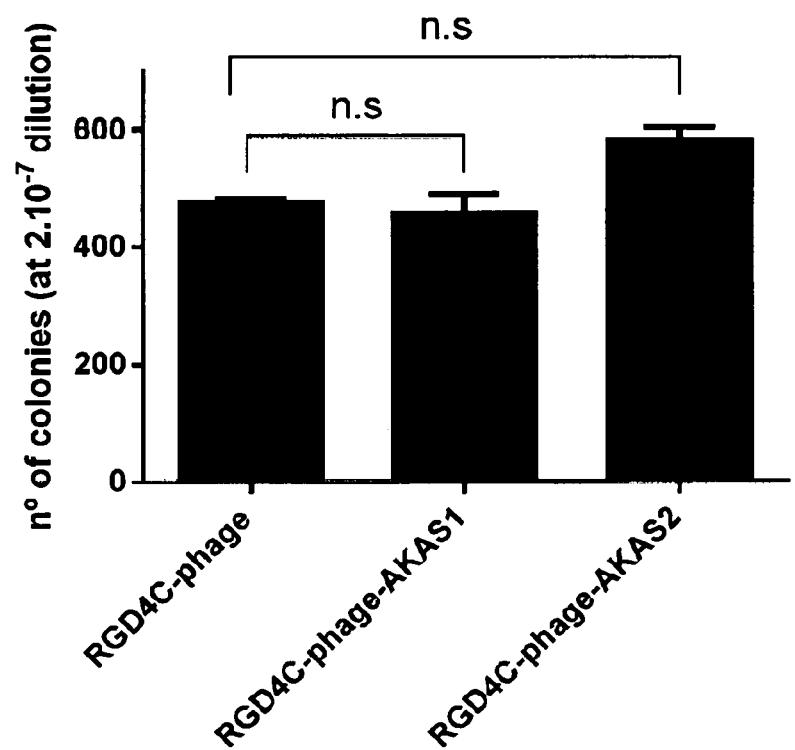
Figure 12B:
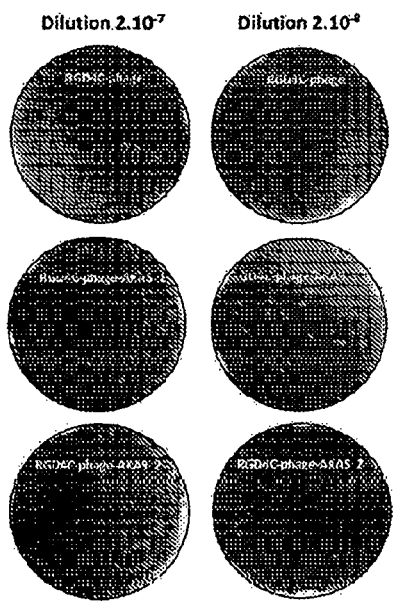
Figure 12C:
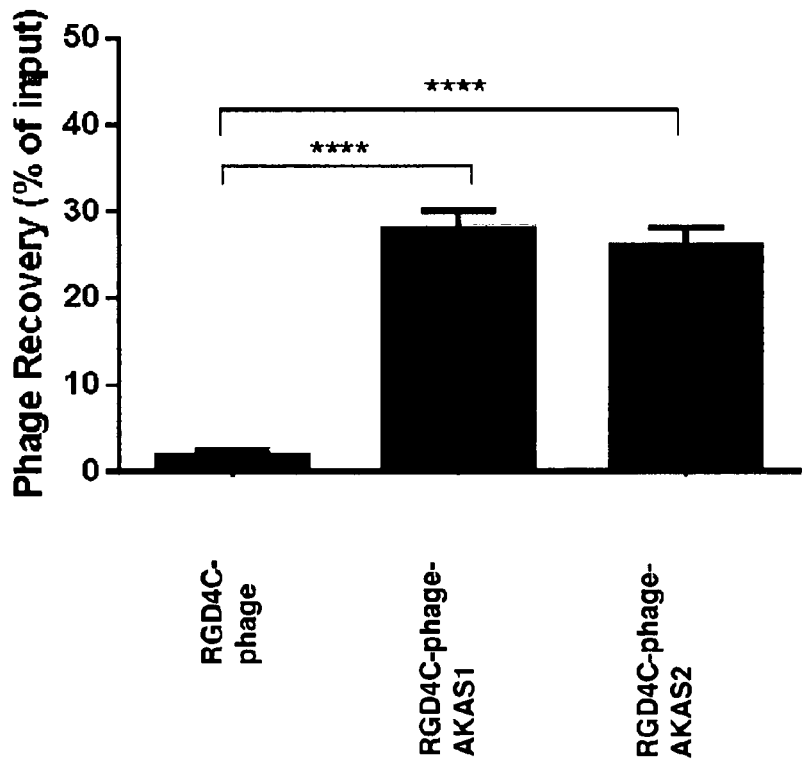

Example 10-Display of the Neutralizing Peptide AKAS Alters the Surface of the Multifunctional Phage, but does not Affect the Phage Titre and Phage Infectivity Next, the inventors wanted to determine whether display of the neutralizing peptide AKAS has an effect on the titre of the produced multifunctional phage particles, and the inventors assessed two RGD4C-phage-AKAS clones (RGD4C-phage-AKAS1 and RGD4C-phage-AKAS2). The inventors infected E. coli K91Kan with several dilutions and the inventors counted the number of colonies after overnight incubation on LB agar plates containing tetracycline. Both multifunctional phage clones (RGD4C-phage-AKAS1 and RGD4C-phage-AKAS2) yielded similar amount of colonies compared to the parental multifunctional phage (FIG. 12a). These data prove that the new multifunctional phage is produced at normal and workable levels. Following the hypothesis that the AKAS peptide should neutralize the negatively-charged phage surface, the inventors carried out an experiment to demonstrate that the new multifunctional phage surface has different physical properties compared to the parental one. Thus, the inventors incubated the RGD4C-phage-AKAS1 and RGD4C-phage-AKAS2 with the DEAE-dextran cationic polymer that associates with negatively charged nucleic acids and proteins. Therefore, less binding was expected with the AKAS phages. After an overnight incubation, the inventors collected the suspension containing the phage particles that didn't attach to the polymer to infect E. coli K91Kan following the same infection assay steps (see materials and methods). As shown in FIG. 12b the number of recovered multifunctional phage RGD4C-phage-AKAS phage was significantly higher than the parental multifunctional phage. After counting the colonies, the inventors determined the phage recovery in terms of percentage of input (FIG. 12c). While the parental RGD4C-phage was almost completely sequestered by the DEAE-dextran polymer, the inventors could recover 30% of the AKAS phages (FIG. 12c). These results clearly show that the surface of the new phage is modified resulting in significant decrease of binding to positively charged molecules.

Example 11—the AKAS-Phages have the Ability to Transduce Cells

As an initial analysis of the phage capacity to transfer genes into mammalian cells, the inventors first transduced rat glioblastoma cells 9L with the parental and the new multifunctional phage carrying the GFP reporter gene. The fluorescence started at day 3 after transduction and pictures were taken day 5 after treatment (FIG. 13 a-d). GFP expression was observed in all the treated cells at overall similar levels. The pictures only show a portion of one well of 9L cells treated with RGD4C-phage (FIG. 13a); RGD4C-phage-AKAS1 (FIG. 13b); and RGD4C-phage-AKAS2 (FIG. 13c). Importantly, there was no GFP expression in cells without phage treatment (FIG. 13d). These qualitative data indicate that the new phages have the intact ability to target and transduce cells.

In order to quantify the levels of transgene expression and compare them with the previous RGD4C-phage, the inventors next used phages expressing the firefly Luc reporter gene to transduce the 9L cells. Luc assay was performed at day 3 post-transduction and the inventors observed similar levels of Luc expression between the 3 phages (FIG. 13e). These results confirm that all phages (parental and new ones) have similar ability to transduce the target cells and that display of the neutralizing AKAS does not affect transgene expression efficiency of the multifunctional phage. Next, the inventors decided to carry out future experiments by testing one AKAS phage only (the RGD4C-phage-AKAS1, termed RGD-phage-AKAS), as both AKAS phages showed similar behaviour in all previous experiments.

Example 12—Phage Incubation with Fibrinogen Decreases the Transduction Levels of RGD4C-Phage while RGD4C-Phage-AKAS Efficacy Remains Intact Furthermore, the inventors explored the phage behaviour in the presence of fibrinogen, a plasma glycoprotein that participates in the blood coagulation, in order to investigate whether the new multifunctional RGD4C-phage-AKAS can avoid non-specific binding to fibrinogen resulting in its sequestration. Recently, it has been shown that fibrinogen plays an important role in the early innate immune response by neutralizing invading pathogens. Moreover, it is deposited with other pro-coagulant molecules into the extracellular matrix of tumour cells serving as a scaffold to support proliferation, migration and tumour cell growth. Thereby, this glycoprotein constitutes an additional obstacle to reach the target tumour cells. As shown from FIG. 14, the inventors transduced the 9L tumour cells with the RGD4C-phage and RGD4C-phage-AKAS under the normal conditions or after 60 minutes of phage incubation with fibrinogen. Consistent with the previous experiments, the data showed no difference in Luc expression in normal transduction conditions (FIG. 14, left bars). However, after incubating the phages with fibrinogen the inventors observed a ~2.2 fold decrease in Luc activity (day 3 post-transduction) in RGD4C-phage-transduced cells compared with RGD4C-phage-AKAS-transduced cells (FIG. 14, right bars). These data show that the multifunctional phage with altered surface is able to avoid non-specific binding to fibrinogen.

Example 13—the RGD4C-Phage-AKAS Phage can Avoid the Anti-Phage Antibody

To uncover further improvement of the features of the novel multifunctional RGD4C-phage-AKAS, the inventors evaluated the effect of an anti-phage polyclonal antibody to neutralize the multifunctional phage and affect the gene transfer efficacy. The inventors treated the 9L tumour cells with the RGD4C-phage and RGD4C-phage-AKAS in the presence of anti-phage antibody (1:8000, Sigma) and the inventors determined the Luc expression after 3 days. The results revealed a significant transduction difference in the presence of the anti-phage antibody, where the RGD4C-phage-AKAS-transduced cells showed an increase ~2.5-fold compared with RGD4C-phage-transduced cells (FIG. 15). These data suggest that the novel phage can skip the neutralizing antibodies against the capsid of the parental multifunctional phage.

Summary

The inventors have designed a multifunctional filamentous phage (see FIG. 1) based on the targeted M13 RGD4C-phage that has the potential to simultaneously carry multiple functions into a single particle, i.e. (i) it displays the targeting ligand on the pIII minor coat protein of the phage for binding to a mammalian protein or receptor; (ii) it serves as a genetic carrier for foreign functional peptides to be displayed on the wild-type pVIII major coat protein in order to operate as a nanoparticle (e.g. nanotube) decorated by hundreds of peptides; (iii) it allows the display of large foreign peptides on the virion surface by the recombinant pVIII protein; and finally (iv) it bears a mammalian transgene cassette inserted in an intergenomic region of the bacteriophage genome for gene expression in mammalian cells.

The inventors showed that all moieties displayed on the RGD4C-phage remain intact and functional in the context of the multifunctional phage by using phage displaying the RGD4C ligand, gold-binding peptide, streptavidin-binding peptide and carrying a mammalian transgene cassette expressing the GFP or Luciferase reporter transgene. In order to assess the potential of the multifunctional phage to promote phage applications, the inventors conducted experiments to assess the effect on gene transfer applications of phage. Thus, they developed the first highly efficient strategy that combines multiple solutions to overcome extracellular and intracellular hurdles to phage gene transfer in one singe phage particle. To show the proof of efficacy of the multifunctional phage in promoting gene transfer by phage, they have generated a multifunctional M13 phage, that carries the targeting ligand on the pIII minor coat protein, displays the H5WYG histidine rich endosome-escape-peptide on the recombinant pVIII major coat protein and expresses a transgene through a mammalian transgene cassette inserted in a non-essential region of the phage genome. Moreover, to overcome the first-rate limiting step of extracellular barrier to phage accessibility to the surface of mammalian cells, hybrid complexes between the multifunctional phage and cationic polymers were generated. The inventors compared the efficacy of the multifunctional phage/polymer to a comprehensive panel of controls including the wild type RGD4C-phage alone, as well as each individual phage either displaying H5WYG peptide or mixed to cationic polymers. The inventors showed that the multifunctional phage/polymer nano-complexes provide substantial transgene expression over all control phage versions while retaining cell targeting and nontoxicity, and that incorporation of cationic polymers generates positively charged phage with enhanced cell surface attachment. Moreover, multifunctional phage/polymer complexes carrying a therapeutic gene produced greater targeted cancer cell killing compared to phage. This new class of targeted hybrid multifunctional platform will advance targeted gene delivery by phage for a broad range of applications, including gene therapy and DNA vaccine.

The invention claimed is:

1. A recombinant targeted bacteriophage for expressing a transgene in a target cell transduced with the bacteriophage, the bacteriophage comprising:
   (i) a first nucleic acid sequence encoding a pIII capsid minor coat protein fused to a cell-targeting ligand for enabling delivery of the bacteriophage to a mammalian target cell;
   (ii) a second nucleic acid sequence encoding at least one wild type pVIII capsid major coat protein for supporting bacteriophage assembly, fused to a foreign peptide of less than ten amino acids;
   (iii) a third nucleic acid sequence encoding a recombinant pVIII capsid major coat protein, which differs in nucleotide sequences from the nucleotide sequence encoding the wild-type pVIII capsid major coat protein, fused to a foreign peptide of more than ten amino acids, wherein the foreign peptide which is displayed on the pVIII capsid major coat protein comprises an endosome escape peptide (EEP), wherein the EEP is displayed on the recombinant pVIII capsid major coat protein; and wherein the endosome escape peptide is H5WYG peptide as set forth in SEQ ID NO: 9; and
   (iv) a mammalian transgene cassette which encodes a protein which exerts a biological effect on the target cell.

2. The bacteriophage according to claim 1, wherein the bacteriophage is F 1, Fd or M13.

3. The bacteriophage according to claim 1, wherein the second nucleic acid sequence encoding a wild-type pVIII capsid major coat protein comprises a nucleotide sequence substantially as set out in SEQ ID No: 1, or wherein the wild-type pVIII capsid major coat protein comprises an amino acid sequence substantially as set out in SEQ ID No: 2.

4. The bacteriophage according to claim 1, wherein the third nucleic acid sequence encoding a recombinant pVIII capsid major coat protein comprises a nucleic acid sequence substantially as set out in SEQ ID No:3, or the recombinant pVIII capsid major coat protein comprises an amino acid sequence substantially as set out in SEQ ID No:4.

5. The bacteriophage according to claim 1, wherein the bacteriophage comprises a nucleic acid sequence substantially as set out in SEQ ID No: 1 and SEQ ID No: 3, or wherein the bacteriophage comprises a wild-type and a recombinant pVIII capsid major coat protein which comprise an amino acid sequence substantially as set out in SEQ ID No: 2 and SEQ ID No: 4.

6. The bacteriophage according to claim 1, wherein the wild type pVIII capsid major coat protein displays a gold-binding peptide, wherein the amino acid sequence of the gold-binding peptide comprises VSGSSPDS as set forth by SEQ ID NO:6.

7. The bacteriophage according to claim 1, wherein the cell-targeting ligand is a tumour-targeting ligand, and wherein the ligand comprises the RGD4C ligand.

8. The bacteriophage according to claim 1, wherein the first nucleic acid sequence encoding the pIII capsid minor coat protein comprises a nucleic acid sequence substantially as set out in SEQ ID No: 7, or wherein the pIII capsid minor coat protein comprises an amino acid sequence substantially as set out in SEQ ID No: 8.

9. The bacteriophage according to claim 1, wherein the foreign peptide which is displayed on the pVIII capsid major coat protein further comprises a nuclear localization signal (NLS) peptide, wherein the NLS peptide is selected from a group consisting of: the large tumour antigen of simian virus 40 (SV40 T antigen as set forth by SEQ ID NO:12); optimized SV40 NLS as set forth by SEQ ID NO:13; the optimized short M9 (osM9) as set forth by SEQ ID NO:14; and a heptamer NLS peptide as set for the by SEQ ID NO:15, wherein the NLS peptide is displayed on the recombinant pVIII capsid major coat protein.

10. The bacteriophage according to claim 1, wherein the wild type pVIII major coat protein of the bacteriophage comprises an N-terminal modification which neutralises the negative charge of the surface of the phage, and results in a net positive charge at physiological pH.

11. The bacteriophage according to claim 10, wherein the modification comprises a tetrapeptide comprising the amino acid sequence AKAS located in the N-terminal of the major coat wild type pVIII protein, and preferably between residues Gly3 and Asp4 of the protein.

12. A vaccine comprising the bacteriophage according to claim 1.

13. A pharmaceutical composition comprising the bacteriophage according to claim 1, and a pharmaceutically acceptable vehicle.

* * * * *

SEQUENCE LISTING

<160> NUMBER OF SEQ ID NOS: 29

<210> SEQ ID NO 1
<211> LENGTH: 222
<212> TYPE: DNA
<213> ORGANISM: Filamentous bacteriophage

<400> SEQUENCE: 1

```
atgaaaaagt ctttagtcct caaagcctcc gtagccgttg ctaccctcgt tccgatgctg      60
tctttcgctg ctgagggtga cgatcccgca aaagcggcct ttgactccct gcaagcctca     120
gcgaccgaat atatcggtta tgcgtgggcg atggttgttg tcattgtcgg cgcaactatc     180
ggtatcaagc tgtttaagaa attcacctcg aaagcaagct ga                        222
```

<210> SEQ ID NO 2
<211> LENGTH: 73
<212> TYPE: PRT
<213> ORGANISM: filamentous bacteriophage

<400> SEQUENCE: 2

```
Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70
```

<210> SEQ ID NO 3
<211> LENGTH: 231
<212> TYPE: DNA
<213> ORGANISM: filamentous bacteriophage

<400> SEQUENCE: 3

```
atgaaaaagt ctttagttct taaagcatct gttgctgttg cgactcttgt tcctatgcta      60
agctttgcca acgtccctgc agaaggtgat gacccggca aagctgcttt tgactctctt      120
caggcttctg ctactgaata catcggctac gcttgggcta tggtggttgt tatcgttggt     180
gctactattg gcatcaaact tttcaaaaaa ttcacttcta aagcgtctta a              231
```

<210> SEQ ID NO 4
<211> LENGTH: 76
<212> TYPE: PRT
<213> ORGANISM: filamentous bacteriophage

<400> SEQUENCE: 4

```
Met Lys Lys Ser Leu Val Leu Lys Ala Ser Val Ala Val Ala Thr Leu
1               5                   10                  15

Val Pro Met Leu Ser Phe Ala Asn Val Pro Ala Glu Gly Asp Asp Pro
            20                  25                  30

Ala Lys Ala Ala Phe Asp Ser Leu Gln Ala Ser Ala Thr Glu Tyr Ile
        35                  40                  45

Gly Tyr Ala Trp Ala Met Val Val Val Ile Val Gly Ala Thr Ile Gly
    50                  55                  60

Ile Lys Leu Phe Lys Lys Phe Thr Ser Lys Ala Ser
65                  70                  75
```

```
<210> SEQ ID NO 5
<211> LENGTH: 15
<212> TYPE: PRT
<213> ORGANISM: Artificial Sequence
<220> FEATURE:
<223> OTHER INFORMATION: Streptavidin-binding peptide

<400> SEQUENCE: 5

Ala Asn Arg Leu Cys His Pro Gln Phe Pro Cys Thr Ser His Glu
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: Gold-binding peptide

<400> SEQUENCE: 6

Val Ser Gly Ser Ser Pro Asp Ser
1               5

<210> SEQ ID NO 7
<211> LENGTH: 1320
<212> TYPE: DNA
<213> ORGANISM: filamentous bacteriophage

<400> SEQUENCE: 7
gtgaaaaaat tattattcgc aattccttta gttgttcctt tctattctca ctcggccgtg      60
gcgtgcgatt gccgcggcga ttgcttctgc ggcgcggggg ccgaaactgt tgaaagttgt     120
ttagcaaaac ctcatacaga aaattcattt actaacgtct ggaaagacga caaaacttta     180
gatcgttacg ctaactatga gggctgtctg tggaatgcta caggcgttgt ggtttgtact     240
ggtgacgaaa ctcagtgtta cggtacatgg gttcctattg gcttgctat ccctgaaaat      300
gagggtggtg gctctgaggg tggcggttct gagggtggcg ttctgaggg tggcggtact      360
aaacctcctg agtacggtga tacacctatt ccgggctata cttatatcaa ccctctcgac     420
ggcacttatc cgcctggtac tgagcaaaac cccgctaatc ctaatccttc tcttgaggag     480
tctcagcctc ttaatacttt catgtttcag aataataggt tccgaaatag cagggtgca      540
ttaactgttt atacgggcac tgttactcaa ggcactgacc ccgttaaaac ttattaccag     600
tacactcctg tatcatcaaa agccatgtat gacgcttact ggaacggtaa attcagagac     660
tgcgctttcc attctggctt taatgaggat ccattcgttt gtgaatatca aggccaatcg     720
tctgacctgc ctcaacctcc tgtcaatgct ggcggcggct ctggtggtgg ttctggtggc     780
ggctctgagg gtggcggctc tgagggtggc ggttctgagg gtggcggctc tgagggtggc     840
ggttccggtg cggctccgg ttccggtgat tttgattatg aaaaaatggc aaacgctaat      900
aagggggcta tgaccgaaaa tgccgatgaa acgcgctac agtctgacgc taaaggcaaa      960
cttgattctg tcgctactga ttacggtgct gctatcgatg gtttcattgg tgacgtttcc    1020
ggccttgcta atggtaatgg tgctactggt gattttgctg gctctaattc ccaaatggct    1080
caagtcggtg acggtgataa ttcaccttta atgaataatt ccgtcaata tttaccttct     1140
ttgcctcagt cggttgaatg tcgcccttat gtctttggcg ctggtaaacc atatgaattt    1200
tctattgatt gtgacaaaat aaacttattc cgtggtgtct ttgcgtttct tttatatgtt    1260
gccaccttta tgtatgtatt ttcgacgttt gctaacatac tgcgtaataa ggagtcttaa    1320
```

<210> SEQ ID NO 8
<211> LENGTH: 438
<212> TYPE: PRT
<213> ORGANISM: filamentous bacteriophage

<400> SEQUENCE: 8

Val Lys Lys Leu Leu Phe Ala Ile Pro Leu Val Val Pro Phe Tyr Ser
1               5                   10                  15

His Ser Val Ala Cys Asp Cys Arg Gly Asp Cys Phe Cys Gly Ala Gly
            20                  25                  30

Ala Glu Thr Val Glu Ser Cys Leu Ala Lys Pro His Thr Glu Asn Ser
        35                  40                  45

Phe Thr Asn Val Trp Lys Asp Asp Lys Thr Leu Asp Arg Tyr Ala Asn
50                  55                  60

Tyr Glu Gly Cys Leu Trp Asn Ala Thr Gly Val Val Cys Thr Gly
65                  70                  75                  80

Asp Glu Thr Gln Cys Tyr Gly Thr Trp Val Pro Ile Gly Leu Ala Ile
            85                  90                  95

Pro Glu Asn Glu Gly Gly Gly Ser Glu Gly Gly Ser Glu Gly Gly
            100                 105                 110

Gly Ser Glu Gly Gly Thr Lys Pro Pro Glu Tyr Gly Asp Thr Pro
            115                 120                 125

Ile Pro Gly Tyr Thr Tyr Ile Asn Pro Leu Asp Gly Thr Tyr Pro Pro
            130                 135                 140

Gly Thr Glu Gln Asn Pro Ala Asn Pro Asn Pro Ser Leu Glu Glu Ser
145                 150                 155                 160

Gln Pro Leu Asn Thr Phe Met Phe Gln Asn Asn Arg Phe Arg Asn Arg
            165                 170                 175

Gln Gly Ala Leu Thr Val Tyr Thr Gly Thr Val Thr Gln Gly Thr Asp
            180                 185                 190

Pro Val Lys Thr Tyr Tyr Gln Tyr Thr Pro Val Ser Ser Lys Ala Met
            195                 200                 205

Tyr Asp Ala Tyr Trp Asn Gly Lys Phe Arg Asp Cys Ala Phe His Ser
210                 215                 220

Gly Phe Asn Glu Asp Pro Phe Val Cys Glu Tyr Gln Gly Gln Ser Ser
225                 230                 235                 240

Asp Leu Pro Gln Pro Pro Val Asn Ala Gly Gly Gly Ser Gly Gly Gly
            245                 250                 255

Ser Gly Gly Gly Ser Glu Gly Gly Ser Glu Gly Gly Ser Glu
            260                 265                 270

Gly Gly Gly Ser Glu Gly Gly Ser Gly Gly Ser Gly Ser Gly
            275                 280                 285

Asp Phe Asp Tyr Glu Lys Met Ala Asn Ala Asn Lys Gly Ala Met Thr
            290                 295                 300

Glu Asn Ala Asp Glu Asn Ala Leu Gln Ser Asp Ala Lys Gly Lys Leu
305                 310                 315                 320

Asp Ser Val Ala Thr Asp Tyr Gly Ala Ala Ile Asp Gly Phe Ile Gly
            325                 330                 335

Asp Val Ser Gly Leu Ala Asn Gly Asn Gly Ala Thr Gly Asp Phe Ala
            340                 345                 350

Gly Ser Asn Ser Gln Met Ala Gln Val Gly Asp Gly Asp Asn Ser Pro
            355                 360                 365

Leu Met Asn Asn Phe Arg Gln Tyr Leu Pro Ser Leu Pro Gln Ser Val
            370                 375                 380

```
Glu Cys Arg Pro Tyr Val Phe Gly Ala Gly Lys Pro Tyr Glu Phe Ser
385                 390                 395                 400

Ile Asp Cys Asp Lys Ile Asn Leu Phe Arg Gly Val Phe Ala Phe Leu
                405                 410                 415

Leu Tyr Val Ala Thr Phe Met Tyr Val Phe Ser Thr Phe Ala Asn Ile
            420                 425                 430

Leu Arg Asn Lys Glu Ser
            435

<210> SEQ ID NO 9
<211> LENGTH: 23
<212> TYPE: PRT
<213> ORGANISM: Artificial Sequence
<220> FEATURE:
<223> OTHER INFORMATION: H5WYG peptide

<400> SEQUENCE: 9

Gly Leu Phe His Ala Ile Ala His Phe Ile His Gly Gly Trp His Gly
1               5                   10                  15

Leu Ile His Gly Trp Tyr Gly
            20

<210> SEQ ID NO 10
<211> LENGTH: 23
<212> TYPE: PRT
<213> ORGANISM: Artificial Sequence
<220> FEATURE:
<223> OTHER INFORMATION: INF7 peptide

<400> SEQUENCE: 10

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 11
<211> LENGTH: 12
<212> TYPE: PRT
<213> ORGANISM: Artificial Sequence
<220> FEATURE:
<223> OTHER INFORMATION: PC1 peptide

<400> SEQUENCE: 11

His Trp Tyr Asp Ser Phe Val Pro Trp Gly His Gln
1               5                   10

<210> SEQ ID NO 12
<211> LENGTH: 7
<212> TYPE: PRT
<213> ORGANISM: Simian virus 40

<400> SEQUENCE: 12

Pro Lys Lys Lys Arg Lys Val
1               5

<210> SEQ ID NO 13
<211> LENGTH: 22
<212> TYPE: PRT
<213> ORGANISM: Simian virus 40

<400> SEQUENCE: 13

Ser Ser Asp Asp Glu Ala Thr Ala Asp Ala Gln His Ala Ala Pro Pro
1               5                   10                  15
```

```
Lys Lys Lys Arg Lys Val
            20

<210> SEQ ID NO 14
<211> LENGTH: 12
<212> TYPE: PRT
<213> ORGANISM: Artificial Sequence
<220> FEATURE:
<223> OTHER INFORMATION: optimized short M9 (osM9) peptide

<400> SEQUENCE: 14

Tyr Asn Asn Gln Ser Ser Asn Arg Gly Pro Tyr Lys
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Heptamer NLS peptide

<400> SEQUENCE: 15

Gln Pro Ser Pro Ser Pro Thr
1               5

<210> SEQ ID NO 16
<211> LENGTH: 42
<212> TYPE: DNA
<213> ORGANISM: Simian virus 40

<400> SEQUENCE: 16
agctttgcca acgtcccgaa aaaaaaacgc aaagtgcctg ca                              42

<210> SEQ ID NO 17
<211> LENGTH: 34
<212> TYPE: DNA
<213> ORGANISM: Simian virus 40

<400> SEQUENCE: 17
ggcactttgc gttttttttt cgggacgttg gcaa                                      34

<210> SEQ ID NO 18
<211> LENGTH: 87
<212> TYPE: DNA
<213> ORGANISM: Simian virus 40

<400> SEQUENCE: 18
agctttgcca acgtcagcag cgatgatgaa gcgaccgcgg atagccagca cgcggcgccg          60
ccgaaaaaaa aacgcaaagt gcctgca                                              87

<210> SEQ ID NO 19
<211> LENGTH: 79
<212> TYPE: DNA
<213> ORGANISM: Simian virus 40

<400> SEQUENCE: 19
ggcactttgc gttttttttt cggcggcgcc gcgtgctggc tatccgcggt cgcttcatca          60
tcgctgctga cgttggcaa                                                       79

<210> SEQ ID NO 20
<211> LENGTH: 57
<212> TYPE: DNA
<213> ORGANISM: Artificial Sequence
```

```
<220> FEATURE:
<223> OTHER INFORMATION: sense nucleotide sequence of short optimized M9
      (osM9) NLS peptide

<400> SEQUENCE: 20
agctttgcca acgtctataa caaccagagc agcaaccgcg gcccgtataa acctgca        57

<210> SEQ ID NO 21
<211> LENGTH: 49
<212> TYPE: DNA
<213> ORGANISM: Artificial Sequence
<220> FEATURE:
<223> OTHER INFORMATION: antisense nucleotide sequence of optimized
      short M9 (osM9) NLS

<400> SEQUENCE: 21
ggtttatacg ggccgcggtt gctgctctgg ttgttataga cgttggcaa                 49

<210> SEQ ID NO 22
<211> LENGTH: 42
<212> TYPE: DNA
<213> ORGANISM: Artificial Sequence
<220> FEATURE:
<223> OTHER INFORMATION: sense nucleotide sequence of heptamer peptide
      NLS

<400> SEQUENCE: 22
agctttgcca acgtccagcc gagcccgagc ccgacccctg ca                        42

<210> SEQ ID NO 23
<211> LENGTH: 34
<212> TYPE: DNA
<213> ORGANISM: Artificial Sequence
<220> FEATURE:
<223> OTHER INFORMATION: antisense nucleotide sequence of heptamer
      peptide NLS peptide

<400> SEQUENCE: 23
ggggtcgggc tcgggctcgg ctggacgttg gcaa                                 34

<210> SEQ ID NO 24
<211> LENGTH: 90
<212> TYPE: DNA
<213> ORGANISM: Artificial Sequence
<220> FEATURE:
<223> OTHER INFORMATION: sense oligonucleotide sequence of H5WYG

<400> SEQUENCE: 24
agctttgcca acgtcggcct gttccatgcg atcgcgcatt tcatccatgg cggctggcat    60
ggcctgatcc atggctggta tggccctgca                                     90

<210> SEQ ID NO 25
<211> LENGTH: 81
<212> TYPE: DNA
<213> ORGANISM: Artificial Sequence
<220> FEATURE:
<223> OTHER INFORMATION: antisense oligonucleotide sequence of H5WYG

<400> SEQUENCE: 25
gggccatacc agccatggat caggccatgc cagccgccat ggatgaaatg cgcgatcgca    60
tggaacaggc cgacgttggc a                                              81

<210> SEQ ID NO 26
<211> LENGTH: 90
<212> TYPE: DNA
```

```
-continued

<213> ORGANISM: Artificial Sequence
<220> FEATURE:
<223> OTHER INFORMATION: sense oligonucleotide sequence of INF7

<400> SEQUENCE: 26
agctttgcca acgtcggcct gttcgaagcg atcgaaggct tcatcgaaaa cggctgggaa      60
ggcatgatcg atggctggta tggccctgca                                       90

<210> SEQ ID NO 27
<211> LENGTH: 82
<212> TYPE: DNA
<213> ORGANISM: Artificial Sequence
<220> FEATURE:
<223> OTHER INFORMATION: antisense oligonucleotide sequence of INF7

<400> SEQUENCE: 27
gggccatacc agccatcgat catgccttcc cagccgtttt cgatgaagcc ttcgatcgct      60
tcgaacaggc cgacgttggc aa                                               82

<210> SEQ ID NO 28
<211> LENGTH: 57
<212> TYPE: DNA
<213> ORGANISM: Artificial Sequence
<220> FEATURE:
<223> OTHER INFORMATION: sense oligonucleotide sequence of PC1

<400> SEQUENCE: 28
agctttgcca acgtccattg gtatgatagc ttcgtgccgt ggggccatca gcctgca        57

<210> SEQ ID NO 29
<211> LENGTH: 49
<212> TYPE: DNA
<213> ORGANISM: Artificial Sequence
<220> FEATURE:
<223> OTHER INFORMATION: antisense oligonucleotide sequence of PC1

<400> SEQUENCE: 29
ggctgatggc cccacggcac gaagctatca taccaatgga cgttggcaa                 49
```